United States Patent [19]

Shimazaki et al.

[11] Patent Number: 5,304,560
[45] Date of Patent: Apr. 19, 1994

[54] QUINAZOLINE DERIVATIVES AND THEIR PREPARATION

[75] Inventors: Norihiko Shimazaki; Hitoshi Yamazaki; Takumi Yatabe, all of Tsukuba; Hirokazu Tanaka, Tsuchiura, all of Japan

[73] Assignee: Fujisawa Pharmaceutical Co., Ltd., Osaka, Japan

[21] Appl. No.: 103,315

[22] Filed: Aug. 9, 1993

Related U.S. Application Data

[63] Continuation of Ser. No. 770,871, Oct. 4, 1991, abandoned.

[30] Foreign Application Priority Data

Oct. 15, 1990 [GB] United Kingdom ................. 9022306
Aug. 27, 1991 [GB] United Kingdom ................. 9118337

[51] Int. Cl.$^5$ ................. A61K 31/505; A61K 31/495; C07D 239; C07D 96; C07D 241/04
[52] U.S. Cl. ..................................... 514/259; 514/253; 544/284; 544/285
[58] Field of Search ................. 544/284, 285; 514/259, 514/253

[56] References Cited

U.S. PATENT DOCUMENTS

| | | | |
|---|---|---|---|
| 3,274,194 | 9/1966 | Hayao . | |
| 4,335,127 | 6/1982 | Vandenberk et al. | 514/259 |
| 4,522,945 | 6/1985 | Vandenberk et al. | 514/259 |
| 4,608,375 | 8/1986 | Ueda et al. | 514/218 |
| 4,705,787 | 11/1987 | Ueda et al. | 514/259 |
| 4,711,883 | 12/1987 | Bandurco et al. | 514/253 |
| 4,716,161 | 12/1987 | Fukami et al. | 514/222 |

FOREIGN PATENT DOCUMENTS 0013612 7/1980 European Pat. Off. .
0129891 1/1985 European Pat. Off. .
017454 8/1982 Japan .

OTHER PUBLICATIONS

Chemical Abstracts, vol. 111, No. 21, Nov. 20, 1989, Columbus, Ohio, USA Cohen et al. "Lack of a difference between ketanserin and ritanserin in Central vs. peripheral serotonin receptor antagonism" p. 70, Column 2, abstract No. 187 437y & Life Sci. 1989, 45(13), 1185–9.

Chemical Abstracts, vol. 101, No. 15, Oct. 8, 1984, Columbus, Ohio, USA A. Nevelsteen et al. "Restoration of post-thrombotic peripheral collateral circulation in the cat by ketanserin, a selective 5-HT2-receptor antagonist" p. 38, col. 1, abstract no. 122 772c & Arch Int. Pharmacodyn. Ther. 1984, 270(2), 268–79.

Chemical Abstracts, vol. 110, No. 13, Mar. 27, 1989, Columbus, Ohio, USA S. Heptinstall, J. Bevan "How can we inhibit 5-HT-in-duced platelet aggregation and why should we bother?" p. 46, column 1, abstract No. 107 881e & Folia Haematol. (Leipzig) 1988, 115(4), 475–8.

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

This invention relates to certain 1-heterocycloalkyl-quinazolin-2,3-dione derivatives, certain pharmaceutically acceptable salts thereof, the process of making those compounds, and the method of using the compounds. The compounds and compositions display effects on the peripheral or central nervous system.

11 Claims, No Drawings

QUINAZOLINE DERIVATIVES AND THEIR PREPARATION

This application is a continuation of application Ser. No. 07/770,871, filed on Oct. 4, 1991, now abandoned.

The present invention relates to novel quinazoline derivatives and pharmaceutically acceptable salts thereof.

More particularly, it relates to novel quinazoline derivatives and pharmaceutically acceptable salts thereof, which display effects on the peripheral or central nervous system, to processes for the preparation thereof, to a pharmaceutical composition comprising the same, to a use of the same as a medicament and to a method of the therapeutic treatment of diseases in a human being or animal.

Accordingly, one object of the present invention is to provide novel quinazoline derivatives and pharmaceutically acceptable salts thereof, which display effects on the peripheral or central nervous system, in particular on the peripheral nervous system.

Another object of the present invention is to provide processes for the preparation of novel quinazoline derivatives and salts thereof.

A further object of the present invention is to provide a pharmaceutical composition comprising, as an active ingredient, said quinazoline derivatives and pharmaceutically acceptable salts thereof.

Still further object of the present invention is to provide a use of said quinazoline derivatives and pharmaceutically acceptable salts thereof as a dopamine receptor agonist and a method of the therapeutic treatment of dopamine receptor mediated diseases, particularly hypertension, cardiovascular disorder (e.g. angina pectoris, myocardial infarction, etc.), Parkinsonism, and the like, in a human being or animal.

The object quinazoline derivatives are novel and can be represented by the following general formula:

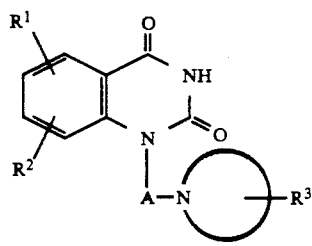

(I)

in which $R^1$ and $R^2$ are each hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, $R^3$ is aryl which may have suitable substituent(s), A is lower alkylene, and the formula:

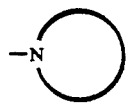

is N-containing heterocyclic group, and pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.); and the like.

According to the present invention, the object compound (I) or pharmaceutically acceptable salts thereof can be prepared by the processes as illustrated by the following reaction schemes.

Process 1:

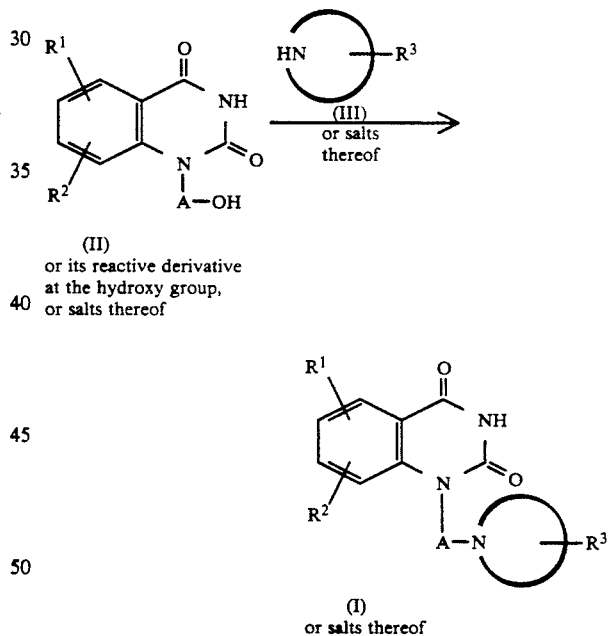

(II)
or its reactive derivative
at the hydroxy group,
or salts thereof (I)
or salts thereof Process 2:

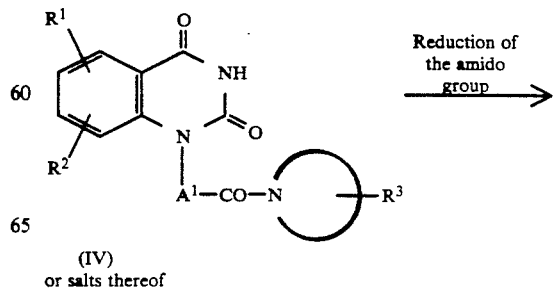

(IV)
or salts thereof

-continued

Process 2:

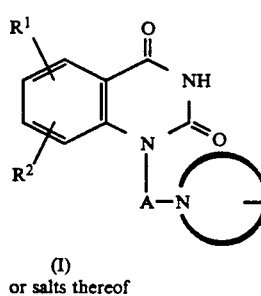

(I)
or salts thereof

Process 3:

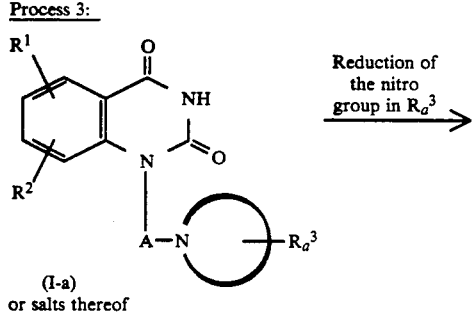

(I-a)
or salts thereof

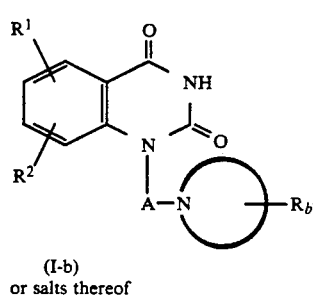

(I-b)
or salts thereof

Process 4:

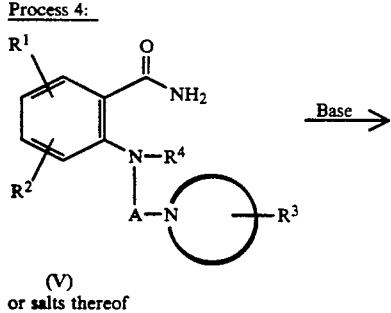

(V)
or salts thereof

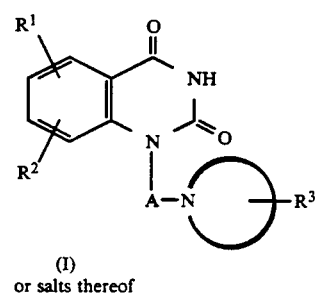

(I)
or salts thereof

Process 5:

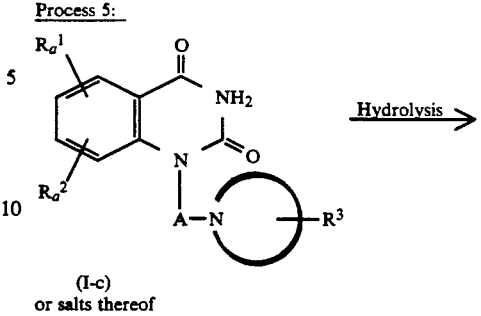

(I-c)
or salts thereof
Hydrolysis →

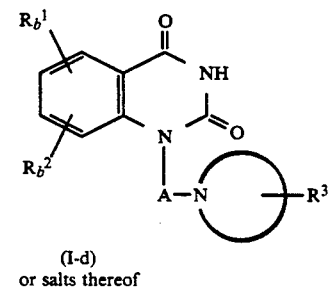

(I-d)
or salts thereof

Process 6:

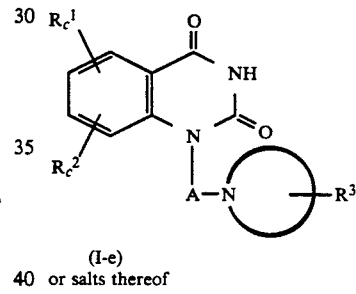

(I-e)
or salts thereof
Reduction of nitro group(s) of $R_c^1$ and/or $R_c^2$ →

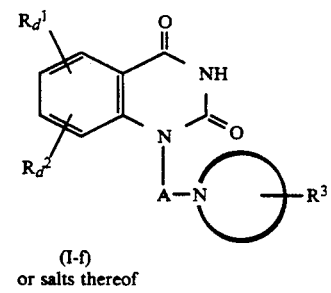

(I-f)
or salts thereof

Process 7:

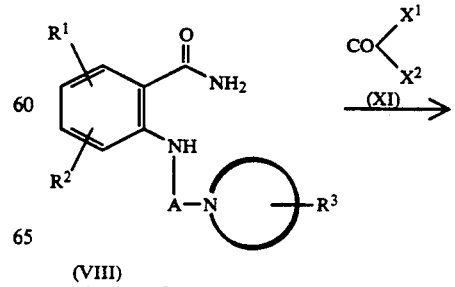

(VIII)
or salts thereof $CO\begin{matrix}X^1\\X^2\end{matrix}$
(XI) →

Base →

Reduction of the nitro group in $R_a^3$ →

Process 7:

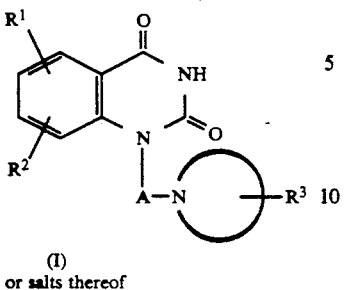

(I)
or salts thereof

Process 8:

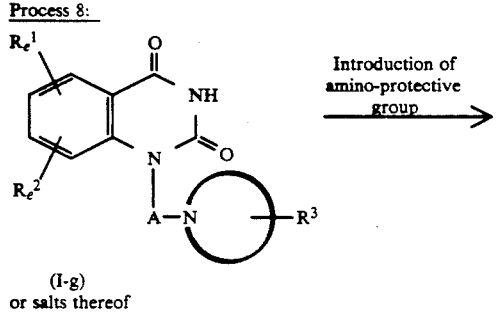

(I-g)
or salts thereof

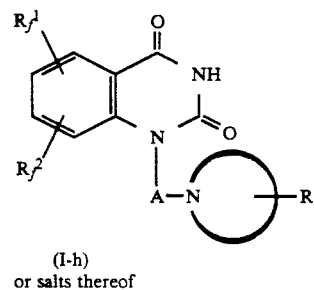

(I-h)
or salts thereof wherein
$R^1$, $R^2$, $R^3$, A and the formula:

are each as defined above, one of $R_a^1$ and $R_a^2$ is lower alkoxy while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, one of $R_b^1$ and $R_b^2$ is hydroxy while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, one of $R_c^1$ and $R_c^2$ is nitro while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, p1 one of $R_d^1$ and $R_d^2$ is hydroxyamino or amino while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, one of $R_e^1$ and $R_e^2$ is amino while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, one of $R_f^1$ and $R_f^2$ is protected amino while the other is hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, $R_a^3$ is aryl substituted by nitro, $R_b^3$ is aryl substituted by amino, $R^4$ is esterified carboxy, $A^1$ is $C_1$-$C_5$ alkylene, and $X^1$ and $X^2$ are each a leaving group.

The starting compounds used in the Processes may be new and can be prepared, for example, by the following methods or a conventional manner.

Method A:

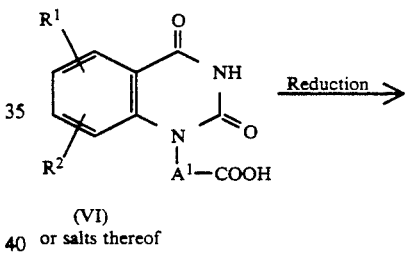

(VI)
or salts thereof

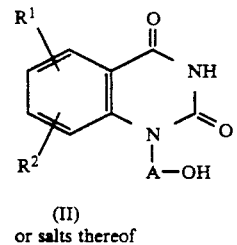

(II)
or salts thereof

Method B:

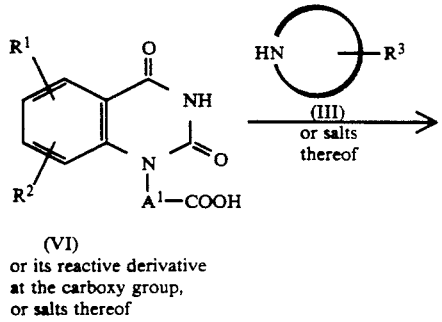

(VI)
or its reactive derivative at the carboxy group,
or salts thereof

Method B:

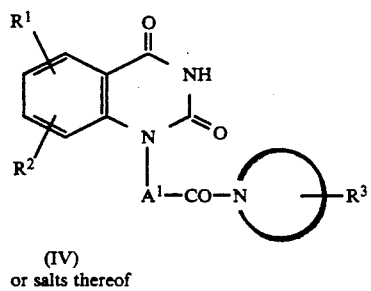

(IV)
or salts thereof

Method C:

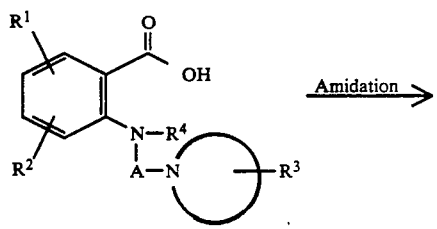

(VII)
or its reactive derivative
at the carboxy group, or
salts thereof

Amidation →

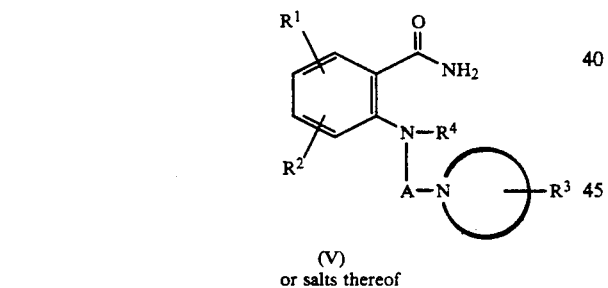

(V)
or salts thereof

Method D:

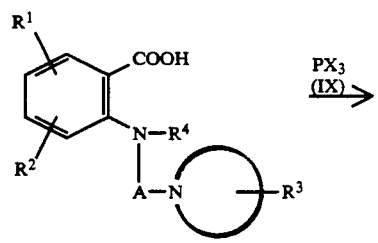

(VII)
or its reactive derivative at
the carboxy group, or salts thereof $PX_3$
(IX) →

Method D:

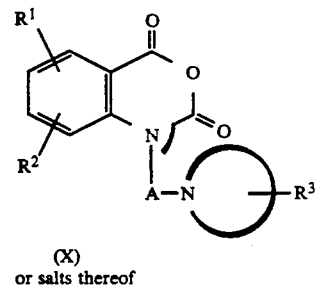

(X)
or salts thereof

Method E:

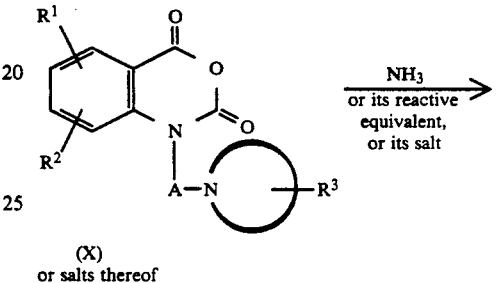

$NH_3$
or its reactive
equivalent,
or its salt
→

(X)
or salts thereof

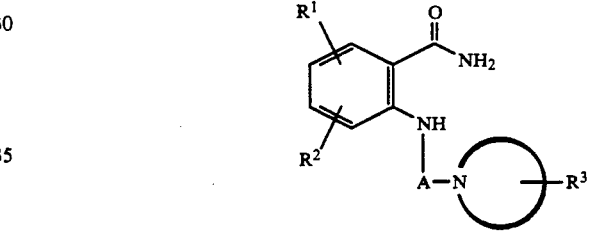

(VIII)
or salts thereof in
which $R^1$, $R^2$, $R^3$, $R^4$, A, $A^1$ and the formula:

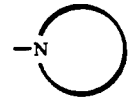

are each as defined above, and
X is a leaving group.

Some of the starting materials of the above Methods are new and can be prepared, for example, according to the method of Preparation as mentioned below, or by a conventional manner.

In the above and subsequent descriptions of the present specification, suitable examples and illustrations of the various definitions which the present invention includes within the scope thereof are explained in detail as follows.

The term "lower" is intended to mean 1 to 6, preferably 1 to 4 carbon atom(s), unless otherwise indicated.

Suitable "lower alkyl" may include straight or branched one such as methyl, ethyl, propyl, isopropyl, butyl, t-butyl, pentyl, hexyl, and the like, in which the most preferable example may be methyl.

Suitable "lower alkoxy" may include straight or branched one such as methoxy, ethoxy, propoxy, isopropoxy, butoxy, t-butoxy, pentyloxy, hexyloxy, and the like, in which the most preferable example may be methoxy and ethoxy for $R^1$ and/or $R^2$, and methoxy, ethoxy and propoxy for the substituent(s) in $R^3$.

Suitable "aryl which may have suitable substituent(s)" may include phenyl, tolyl, xylyl, cumenyl, mesithyl, naphthyl, and the like, each of which may be substituted by one or more, preferably one to three, more preferably one or two substituent(s) such as halogen (e.g. fluorine, chlorine, bromine, iodine), lower alkyl as mentioned above (e.g. methyl, etc.), lower alkoxy as mentioned above (e.g. methoxy, ethoxy, propoxy, etc.), amino, nitro, and the like, in which more preferred example may be phenyl which is substituted or unsubstituted by a group consisting of halogen, $C_1$–$C_4$ alkyl, $C_1$–$C_4$ alkoxy, nitro and amino, and the most preferred one may be phenyl, 2-(or 4-)tolyl, 2-(or 4-)-chlorophenyl, 2-methoxyphenyl, 2-ethoxyphenyl, 2-propoxyphenyl, 2-nitrophenyl and 2-aminophenyl.

Suitable "aryl substituted by nitro" and "aryl substituted by amino" means aforementioned "aryl which may have suitable substituent(s)", in which said aryl is substituted by nitro and amino respectively.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower-)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2- or )pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(-lower)alkyl ester, or (5-lower alkyl-2-oxo-1,3-dioxol-4-yl)[lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester [e.g. mono- or di- or triphenyl(lower)alkyl ester, etc.] which may have at least one suitable substituent(s) (e.g. lower alkoxy, nitro, hydroxy, lower alkyl, etc.), for example, mono- or di- or triphenyl($C_1$–$C_4$)alkyl ester which may have ($C_1$–$C_4$)alkoxy [e.g. benzyl ester, benzhydryl ester, trityl ester, phenethyl ester, 4-methoxybenzyl ester, 3,4-dimethoxybenzyl ester, bis(methoxyphenyl)methyl ester, etc.], nitrophenyl($C_1$–$C_4$)alkyl ester (e.g. 4-nitrobenzyl ester, etc.), [hydroxy]-($C_1$–$C_4$)alkylphenyl($C_1$–$C_4$)alkyl ester (e.g. 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_1$–$C_4$ alkoxycarbonyl and the most preferable one may be methoxycarbonyl.

Suitable "esterified carboxy" may be the same one as mentioned in the explanation of "protected carboxy" in which the most preferred example may be ethoxycarbonyl.

Suitable "protected amino" may include amino protected by a conventional amino-protective group as mentioned below.

Suitable "amino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroar(lower)alkoxycarbonyl(e.g. nitrobenzyloxycarbonyl, etc.), and the like.

More preferable example of amino-protective group may be aliphatic acyl such as lower alkylsulfonyl and the most preferable one may be methanesulfonyl.

More preferable example of protected amino thus defined may be aliphatic acylamino such as lower alkylsulfonylamino and the most preferable one may be methanesulfonylamino.

Suitable "halogen" may be fluorine, chlorine, bromine, iodine, and more preferred example may be chlorine and fluorine.

Suitable "lower alkylene" may include straight or branched one such as methylene, ethylene, trimethylene, tetramethylene, pentamethylene, hexamethylene, methylmethylene, ethylethylene, propylene, and the like, in which more preferred example may be $C_1$–$C_4$ alkylene and the most preferred one may be tetramethylene.

Suitable "$C_1$–$C_5$ alkylene" means aforementioned "lower alkylene" except for $C_6$ alkylene, in which more preferred example may be $C_1$–$C_4$ alkylene and the most preferred one may be trimethylene.

Suitable "leaving group" may include imidazole, lower alkylimidazole (e.g. 2-methylimidazole, etc.), an acid residue such as halogen as mentioned above (e.g. chlorine, etc.), sulfonyloxy (e.g. mesyloxy, tosyloxy, etc.), trihalo(lower)alkyloxy (e.g. trichloromethoxy, etc.) and the like.

Suitable "lower alkylthio" may include straight or branched one such as methylthio, ethylthio, propylthio, isopropylthio, butylthio, t-butylthio, pentylthio, hexylthio, and the like.

Suitable "N-containing heterocyclic group" means saturated or unsaturated, monocyclic or polycyclic heterocyclic group containing at least one nitrogen atom and optionally other hetero-atom(s) such as an oxygen, sulfur, nitrogen atom and the like, and said heterocyclic group is attached to A at the ring nitrogen atom.

Preferable N-containing heterocyclic group may be:
unsaturated 3 to 8-membered, preferably 5- or 6-membered heteromonocyclic group containing 1 to 4 nitrogen atom(s), for example, pyrrol-1-yl, pyrrolin-1-yl, imidazol-1-yl, pyrazol-1-yl, tetrahydropyridyl (e.g. 1,2,3,6-tetrahydropyridin-1-yl, etc.), triazolyl, (e.g. 4H-1,2,4-triazol-4-yl, 1H-1,2,3-triazol-1-yl, 2H-1,2,3-triazol-2-yl, etc.), tetrazolyl (e.g. 1H-tetrazol-1-yl, 2H-tetrazol-2-yl, etc.), dihydrotriazinyl (e.g. 4,5-dihydro-1,2, -triazin-4-yl, 2,5-dihydro-1,2,4-triazin-2-yl, etc.), etc.;

saturated 3 to 8-membered, preferably 5- or 6-membered heteromonocyclic group containing 1 to 4 nitrogen atom(s), for example, azetidin-1-yl, pyrrolidin-1-yl, imidazolidin-1-(or 3-)yl, piperidin-1-yl, pyrazolidin-1-yl, piperazin-1-yl, etc.;

unsaturated 3 to 8-membered, preferably 5- or 6-membered heteromonocyclic group containing 1 to 2 oxygen atom(s) and 1 to 3 nitrogen atom(s), for example, oxazinyl (e.g. 4H-1,4-oxazin-4-yl, etc.), oxadiazinyl (e.g. 4H-1,2,4-oxadiazin-4-yl, etc.), saturated 3 to 8-membered, preferably 5- or 6-membered heteromonocyclic group containing 1 to 2 oxygen atom(s) and 1 to 3 nitrogen atom(s), for example, morpholin-4-yl, etc.;

unsaturated 3 to 8-membered, preferably 5- or 6-membered heteromonocyclic containing 1 to 2 sulfur atom(s) and 1 to 3 nitrogen atom(s), for example, thiazolinyl (e.g. 1,3-thiazolin-3-yl, 1,2-thiazolin-2-yl, etc), etc.

saturated 3 to 8-membered, preferably 5- or 6-membered heteromonocyclic group containing 1 to 2 sulfur atom(s) and 1 to 3 nitrogen atoms(s), for example, thiazolidinyl e.g. 1,3-thiazolidin-1,2-thiazolidin-2-yl, etc.], etc.;

wherein more preferred example may be saturated or unsaturated 5- or 6-membered heteromonocyclic group containing 1 to 4 nitrogen atom(s), and the most preferable one may be piperazin-1-yl and 1,2,3,6-tetrahydropyridin-1-yl.

Preferable embodiments of $R^1$, $R^2$, $R^3$, A and the formula

are as follows:

$R^1$ and $R^2$ are each hydrogen, halogen, nitro, amino, protected amino, hydroxyamino, lower alkoxy, lower alkyl, hydroxy, sulfamoyl, carboxy, protected carboxy, carbamoyl, mercapto or lower alkylthio, $R^3$ is aryl which may have suitable substituent(s), A is lower alkylene, and the formula:

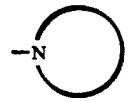

is N-containing heterocyclic group.

Further, preferable embodiments of $R^1$, $R^2$, $R^3$, A and the formula

are as follows:

$R^1$ and $R^2$ are each hydrogen, halogen, nitro, amino, acylamino such as lower alkylsulfonyl (e.g. methylsulfonyl, ethylsulfonyl, etc.), hydroxyamino, lower alkoxy, lower alkyl, hydroxy, sulfamoyl, carboxy, esterified carboxy such as lower alkoxycarbonyl, carbamoyl, mercapto, lower alkylthio or imidazolyl, $R^3$ is phenyl which is substituted or unsubstituted by one to three substituent(s) selected from the group consisting of halogen, lower alkyl, lower alkoxy, nitro and amino, A is lower alkylene, and
the formula

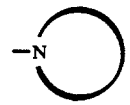

is saturated or unsaturated 5- or 6-membered heteromonocyclic group containing 1 to 4 nitrogen atom(s) such as piperazin-1-yl and 1,2,3,6-tetrahydropyridin-1-yl, and the like.

The processes for the preparation of the object compound (I) of the present invention are explained in detail in the following.

(1) Process 1:

The compound (I) or salts thereof can be prepared by reacting the compound (II) or its reactive derivative at the hydroxy group, or salts thereof with the compound (III).

Suitable salts of the compound (II) may be the same as those for the compound (I).

Suitable salts of the compound (III) may be the same as acid addition salts such as those given for the compound (I).

Suitable reactive derivative at the hydroxy group of the compound (II) may include halide (e.g. chloride, bromide, iodide, etc.), sulfonate (e.g. methanesulfonate, benzenesulfonate, p-toluenesulfonate, etc.), and the like.

This reaction is usually carried out in the presence of an inorganic base such as an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), alkaline earth metal carbonate (e.g. magnesium carbonate, calcium carbonate, etc.), an alkali metal bicarbonate (e.g. sodium bicarbonate, potassium bicarbonate, etc.), etc; an organic base such as trimethylamine, triethylamine, dicyclohexylamine, pyridine, picoline, lutidine, N-ethyl-N,N-diisopropylamine, etc.

This reaction can be carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from warming to heating.

(2) Process 2:

The compound (I) or salts thereof can be prepared by reducing the amido moiety of the compound (IV) or salts thereof.

Suitable salts of the compound (IV) may be the same as those for the compound (I).

The reduction method applicable for this removal reaction may include a conventional one which is capable of converting the amido group into the aminomethyl group, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); a conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.); lithium aluminum hydride; sodium borohydride, a combination of tri(lower)alkylborane and sodium borohydride; borane, diborane, a combination of sodium borohydride and borone trifluoride; and the like, in which more preferable method is lithium aluminum hydride, borane, diborane, and a combination of sodium borohydride and borone trifluoride.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(3) Process 3:

The compound (I-b) or salts thereof can be prepared by subjecting the compound (I-a) or salts thereof to a reduction of the nitro group in $R_3{}^a$.

Suitable salts of the compounds (I-a) and (I-b) may be the same as those for the compound (I).

The present reaction is usually carried out by a conventional method as mentioned below.

Reduction method:

The reduction method applicable for this reaction may include conventional ones which are capable of converting a nitro group to a hydroxyamino or amino group, for example, reduction using tin(II) chloride or zinc powder; reduction using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.); reduction using aluminum amalgam; electrolytic reduction; and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from warming to heating.

(4) Process 4:

The compound (I) or salts thereof can be prepared by reacting the compound (V) or salts thereof with a base.

Suitable salts of the compound (VII) may be the same as those for the compound (I).

Suitable base used in this reaction may be the same ones as mentioned in Process 5.

This reaction can be carried out in a conventional solvent which does not adversely influence the reaction such as alcohol (e.g. methanol, ethanol, etc.), dichloromethane, pyridine, N,N-dimethylformamide, 4-methyl-2-pentanone, tetrahydrofuran, etc., or a mixture thereof.

The reaction temperature is not critical and the reaction is usually carried out under from warming to heating.

(5) Process 5:

The compound (I-d) or salts thereof can be prepared by hydrolyzing the compound (I-c) or salts thereof.

Suitable salts of the compounds (I-c) and (I-d) may be the same as those for the compound (I).

The hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(6) Process 6:

The compound (I-f) or salts thereof can be prepared by subjecting the compound (I-e) or salts thereof to a reduction of the nitro group(s) of $R_c^1$ and/or $R_c^2$.

Suitable salts of the compounds (I-e) and (I-f) may be the same as those for the compound (I).

The method of reduction and the reaction conditions (e.g. reaction temperature, solvent, etc.) are substantially the same as those illustrated in Process 3, and therefore are to be referred to said explanation.

(7) Process 7:

The compound (I) or salts thereof can be prepared by reacting the compound (VIII) or salts thereof with the compound (XI).

Suitable salts of the compound (VIII) may be the same as those for the compound (I).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof.

The reaction temperature is not critical and the reaction is usually carried out under from warming to heating.

In this reaction, when at least one of $R^1$ and $R^2$ is halogen and the compound (XI) is carbonyldiimidazole, at least one of $R^1$ and $R^2$ may be converted into imidazol-1-yl group in the object compound (I) during the reaction.

(8) Process 8:

The compound (I-h) or salts thereof can be prepared by introducing an amino-protective group into the compound (I-g) or salts thereof.

Suitable salts of the compounds (I-g) and (I-h) may be the same as those for the compound (I).

Suitable introducing agent of an amino-protective group is a conventional one such as an acylating agent of an amino group such as an organic carboxylic, carbonic, sulfonic and carbamic acid or its conventional reactive derivatives.

This reaction is usually carried out in the presence of an inorganic base such as an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), alkaline earth metal carbonate (e.g. magnesium carbonate, calcium carbonate, etc.), an alkali metal bicarbonate (e.g. sodium bicarbonate, potassium bicarbonate, etc.), etc; an organic base such as trimethylamine, triethylamine, dicyclohexylamine, pyridine, picoline, lutidine, N-ethyl-N,N-diisopropylamine, etc.

Further, this reaction can be carried out in the presence of a conventional condensing agent used for a so-called "acylation", when the introducing agent of an amino-protective group is in a free acid form.

This reaction can be carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from cooling to warming The object compounds obtained according to the above Processes can be isolated and purified in a conventional manner, for example, extraction, precipitation, fractional crystallization, recrystallization, chromatography, and the like.

Methods for preparing the new starting compound or salts thereof used in the above processes are explained in detail in the following.

(A) Method A:

The compound (II) or salts thereof can be prepared by reducing the compound (VI) or salts thereof.

Suitable salts of the compound (VI) may be the same as those for the compound (I).

The method of reduction and the reaction conditions (e.g. reaction temperature, solvent, etc.) are substantially the same as those illustrated in Process 2, which are capable of converting the carboxy group into the hydroxymethyl group, and therefore are to be referred to said explanation.

(B) Method B:

The compound (IV) or salts thereof can be prepared by reacting the compound (VI) or its reactive derivative at the carboxy group, or salts thereof with the compound (III).

Suitable reactive derivative at the carboxy group of the compound (VI) may include acid halide (e.g. acid chloride, acid bromide, acid iodide, etc.), an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. succinimido ester, cyanomethyl ester methoxymethyl ester, dimethyliminiomethyl [$(CH_3)_2N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p- nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected among them according to the kind of the compound (VI) to be used.

This reaction is usually carried out in the presence of an inorganic base such as an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), alkaline earth metal carbonate (e.g. magnesium carbonate, calcium carbonate, etc.), an alkali metal bicarbonate (e.g. sodium bicarbonate, potassium bicarbonate, etc.), etc; an organic base such as trimethylamine, triethylamine, dicyclohexylamine, pyridine, picoline, lutidine, N-ethyl-N,N-diisopropylamine; etc.

This reaction can be carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from cooling to warming.

(C) Method C:

The compound (V) or salts thereof can be prepared by amidating the compound (VII) or its reactive derivative at the carboxy group, or salts thereof.

Suitable reactive derivative at the carboxy group of the compound (VII) may be the same ones as mentioned in Method B.

Suitable amidating agent used in this reaction may include a conventional one which is capable of converting the carboxy group into the amido group such as ammonia or acid addition salts thereof (e.g. ammonium chloride, etc.), and the like.

This reaction can be carried out in the presence of a such base as mentioned in Method C.

This reaction can be carried out in a conventional solvent which does not adversely influence the reaction such as dichloromethane, pyridine, N,N-dimethylformamide, 4-methyl-2-pentanone, tetrahydrofuran, acetonitrile, etc., or a mixture thereof.

The reaction temperature is not critical and the reaction is usually carried out under from cooling to warming.

(D) Method D:

The compound (X) or salts thereof can be prepared by reacting the compound (VII) or its reactive derivative at the carboxy group, or salts thereof with the compound (IX).

Suitable salts of the compound (X) may be the same as those for the compound (I).

This reaction can be carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from warming to heating.

(E) Method E:

The compound (VIII) or salts thereof can be prepared by reacting the compound (X) or salts thereof with ammonia or its reactive equivalent, or its salt.

Suitable reactive equivalent of ammonia may be a conventional one and include ammonium hydroxide, and the like.

Suitable salt of ammonia may be acid addition salt such as ammonium chloride, and the like.

This reaction can be carried out in a conventional solvent which does not adversely influence the reaction such as dichloromethane, pyridine, N,N-dimethylformamide, 4-methyl-2-pentanone, tetrahydrofuran, acetonitrile, etc., or a mixture thereof.

The reaction temperature is not critical and the reaction is usually carried out under from cooling to warming.

The object quinazoline derivatives (I) stimulate presynaptic(neuronal) and/or postsynaptic(vascular) dopamine receptors that mediate inhibition of neurogenic release of catecholamine and/or dilatation of renal vasculature and remission of parkinsonism, respectively. Quinazoline derivatives (I) effect on the cardiovascular system as a consequence of its interaction with dopaminergic and adrenergic receptors.

The object compound (I) and pharmaceutically acceptable salts thereof of the present invention are novel and display dopamine receptor stimulating effects; 5-HT receptor antagonism, especially 5-HT$_2$ receptor antagonism; $\alpha_1$ receptor antagonism; and the like, and are useful as a dopamine receptor agonist; 5-HT receptor antagonist, especially 5-HT$_2$ receptor antagonist; $\alpha_1$ receptor antagonist; and the like, for treating or preventing hypertension such as renal hypertension and other cardiovascular disorders (e.g. angina pectoris, congestive heart failure, myocardial infarction, etc.); Parkinsonism; hyperprolactinemia; disorders of peripheral perfusion such as Raynaud's phenomenon, Burger's diseases, and intermittent claudication; thrombotic and/or smooth muscle cell proliferative disease such as restenosis after percutaneous transluminal coronary angioplasty; hypercholesterolemia, hyperlipemia; urinary disturvance; and the like.

The compound (I) and pharmaceutically acceptable salts thereof may be also useful as an adrenolytic, tranquilizer, sedative, anti-emetic, hypothermic, skeletal muscle relaxant, anti-inflammatory, hypoglycemic antiviral, or blood flow increasing agent.

Now in order to show the utility of the object compound (I) and pharmaceutically acceptable salts, the test data on dopamine receptor stimulating effects of the representative compound of the compound (I) of this invention are shown in the following.

Test 1 [Dopamine receptor (DA$_2$ receptor) binding assay]

Test Method 1:

The affinity for DA$_2$ receptor of a Test Compound was determined following in vitro receptor binding assays.

Male rats weighing 150–300 g were decapitated and the stratum were dissected from their brains. The tissue was homogenized in 30 volumes of buffer which consisted of 50 mM Tris-HCl (pH 7.4 at 25° C.), 120 mM sodium chloride, 5 mM potassium chloride, 1 mM calcium chloride, 1 mM magnesium chloride, 10 μM pargirine, and 0.1% ascorbic acid. The homogenate was centrifuged at 50,000 g for 15 minutes. The pellet was resuspended in 30 volumes of the buffer. The tissue suspension was centrifuged and suspended again in the same way.

Incubation tubes received 100 μl of [phenyl-4-$^3$H]spiperone, 100 μl of the Test Compound and 0.8 ml of tissue suspension during binding assays. The concentration of [phenyl-4-$^3$H]spiperone was 0.2 nM. The final tissue concentration of rat striatum was 160 μg/ml. The tubes were incubated at 37° C. for 10 minutes, and then filtered under vacuum through Whatman GF/B filters and washed three times with 3 ml of ice-cold buffer. The filters were counted by liquid scintillation counter.

Specific binding of the [$^3$H]spiperone was determined in the presence of 1 μM butaclamol. The IC$_{50}$ value of the Test Compound was calculated from the data of [$^3$H]spiperone binding in the presence of $10^{-9}$M, $10^{-8}$M, $10^{-7}$M and $10^{-6}$M Test Compound.

Test Compound:
Compound A [The product of Example 6]
Test Result 1:

| Test Compound | IC$_{50}$ (M) |
|---|---|
| Compound A | 7.4 × $10^{-9}$ |

Test 2 [Inhibition of reserpine-induced DOPA accumulation]

Test Method 2:
Male SD rats weighing 300–400 g were used in this test. Rats were pretreated with reserpine (1 mg/kg, S.C.) 17–19 hours before sacrifice and then fasted. Test Compound was given orally to the rats 2 hours before sacrifice. [m-Hydroxybenzylhydrazine (100 mg/kg, i.p.) was given 30 minutes before sacrifice.] Each rat was exposed to microwaves using a head-focus microwave applicator for 1.5 seconds. The whole brain was removed and further separated into the striatum.

DOPA was determined as follows; the striatum was homogenized in 9 volumes of 0.1N perchloric acid solution (0.4% EDTA·2Na). The homogenate was centrifuged at 10,000 rpm for 1 minutes. The supernatant was applied to high performance liquid chromatography.

Test Result 2

| Test Compound | dose (mg/kg) | Inhibition (%) |
|---|---|---|
| Compound A | 3.2 | 10 |

Test 3 [Hypotensive effect on spontaneous hypertensive rats]

Test Method 3:
15 to 25-Week-old male spontaneous hypertensive rats with mean arterial blood pressure of about 160–200 mmHg, weighing 300–350 g, were used. The animals were cannulated in the left femoral artery and the mean blood pressure and heart rate were measured with a pressure-transducer. The animals were deprived of food for about 18 hours before oral dosing. The Test Compound was suspended in 0.5% methylcellulose, and given orally.

Test Result 3:

The maximum decrease of blood pressure (%) is shown in Table.

| Test Compound | dose (mg/kg) | Maximum decrease of blood pressure (%) |
|---|---|---|
| Compound A | 1 | 19 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between about 0.001 mg and about 300 mg, preferably about 0.1 mg to about 50 mg per day may be administered to a patient. An average single dose of about 0.001 mg, 0.01 mg, 0.03 mg, 0.1 mg, 0.3 mg, 0.6 mg, 1.0 mg, 3.0 mg, 10.0 mg, 50.0 mg, 100.0 mg, of the object compound (I) of the present invention may be used as adrenolytic, hypotensive, cardiovascular, tranquilizer, sedative, anti-emetic, hypothermic, skeletal muscle relaxant, anti-inflammatory, and anti-viral agents.

The following Preparations and Examples are given for the purpose of illustrating this invention in more detail.

Preparation 1-1)
A mixture of 2,4(1H,3H)-quinazolinedione (1.62 g), 1,1,1,3,3,3-hexamethyldisilazane (3.54 g) and ammonium sulfate (160 mg) in toluene (5 ml) was refluxed for 3 hours. After toluene and excess 1,1,1,3,3,3-hexamethyldisilazane were evaporated in vacuo, ethyl 4-bromocrotonate (3.84 g) was added thereto. The mixture was heated to 120° C. After 3 hours, the reaction mixture was cooled below 100° C., and ethanol was added. Crystallized materials were collected and washed with ethanol to give 1-(3-ethoxycarbonyl-2-propenyl)-2,4-(1H,3H)-quinazolinedione (1.95 g).

NMR (CDCl$_3$, δ): 1.25 (3H, t, J=6 Hz), 4.20 (2H, q, J=6 Hz), 4.90 (2H, dd, J=2, 3 Hz), 5.90 (1H, td, J=1.5, 13 Hz), 6.95–7.10 (2H, m), 7.25–7.35 (1H, m), 7.70 (1H, dt, J=1.5, 7 Hz), 8.25 (1H, dd, J=1, 7 Hz), 9.00 (1H, br s)

Preparation 1-2)
To a solution of 1-(3-ethoxycarbonyl-2-propenyl)-2,4-(1H,3H)-quinazolinedione (5.50 g) in tetrahydrofuran-methanol (200 ml, 3:1 V/V) was added 10% palladium on carbon (550 mg). The mixture was stirred vigorously under atmospheric pressure of hydrogen. After 6 hours, the catalyst was filtered off, and the solvent was evaporated. 1-(3-Ethoxycarbonylpropyl)-

2,4(1H,3H)-quinazolinedione (5.24 g) as a crystal was obtained by recrystallization from ethanol.

NMR (CDCl$_3$, δ): 1.30 (3H, t, J=6 Hz), 1.95–2.05 (2H, m), 2.50 (2H, t, J=5 Hz), 4.10–4.25 (4H, m), 7.30 (1H, t, J=7 Hz), 7.50 (1H, d, J=7 Hz), 7.75 (1H, dt, J=1, 7 Hz), 8.25 (1H, dd, J=1, 7 Hz), 9.00 (1H, br s)

Preparation 1-3)

A mixture of 1-(3-ethoxycarbonylpropyl)-2,4(1H,3H)-quinazolinedione (552 mg) and 1N sodium hydroxide (6.0 ml) in methanol-tetrahydrofuran (26 ml, 3.3:1 V/V) was stirred for 3 hours at room temperature. After evaporation of the organic solvents, the mixture was adjusted to pH 4~5 with 1N hydrochloric acid to give precipitates. Collected precipitates were washed in turn with water and ethanol to give 1-(3-carboxypropyl)-2,4(1H,3H)-quinazolinedione (393 mg) as a powder.

NMR (DMSO-d$_6$, δ): 1.70–1.95 (2H, m), 2.40 (2H, t, J=6 Hz), 4.05 (2H, t, J=6 Hz), 7.30 (1H, t, J=6 Hz), 7.55 (1H, d, J=7 Hz), 7.80 (1H, dt, J=1.5, 6 Hz), 8.00 (1H, dd, J=1.5, 6 Hz)

Preparation 1-4)

To a stirred suspension of 1-(3-carboxypropyl)-2,4(1H,3H)-quinazolinedione (2.00 g) in tetrahydrofuran (40 ml) was added 1M borane in tetrahydrofuran (24.2 ml) on an ice-bath, and the mixture was stirred for additional 2 hours at room temperature. The reaction mixture was quenched with 1N hydrochloric acid, and the organic solvent was evaporated. The residue was triturated with water, filtered and washed in turn with water and ethyl ether to give 1-(4-hydroxybutyl)-2,4(1H,3H)-quinazolinedione (1.74 g) as a crystal.

NMR (DMSO-d$_6$, δ): 1.45–1.70 (4H, m), 3.30–3.50 (3H, m), 4.05 (2H, t, J=7 Hz), 4.50 (1H, t, J=5 Hz), 7.30 (1H, t, J=6 Hz), 7.50 (1H, d, J=6 Hz), 7.80 (1H, dt, J=1.5, 5 Hz), 8.05 (1H, dd, J=1.5, 5 Hz)

Preparation 1-5)

A mixture of 1-(4-hydroxybutyl)-2,4(1H,3H)-quinazolinedione 290 mg), thionyl chloride (0.54 ml), and pyridine (98 mg) in tetrahydrofuran (10 ml) was refluxed for 2 hours. After evaporation of the solvents, the residue was dissolved in chloroform, washed in turn with water, saturated sodium bicarbonate and brine, dried over magnesium sulfate, and evaporated. Crude material was crystallized from ethyl ether-isopropyl ether to give 1-(4-chlorobutyl)-2,4(1H,3H)-quinazolinedione (226 mg) as a powder.

NMR (CDCl$_3$, δ): 1.85–2.00 (4H, m), 3.65 (2H, t, J=4 Hz), 4.10–4.25 (2H, m), 7.20–7.35 (2H, m), 7.75 (1H, dt, J=1.5, 7 Hz), 8.25 (1H, dd, J=1.5, 7 Hz), 8.80 (1H, br s)

Preparation 2-1)

To a stirred solution of 2,4-dioxo-1H-3,1-benzoxazine (2.00 g) in dry dimethylformamide (20 ml) was added sodium hydride (540 mg, 60% oil suspension) in several portions on an ice-bath. After 30 minutes, ethyl 4-bromocrotonate (3.79 g) was added to the mixture. After stirring for additional 2 hours at room temperature, 28% ammonium hydroxide (7.5 ml) was added on an ice-bath. The mixture was stirred for 30 minutes at the same temperature, neutralized with 1N hydrochloric acid, extracted with ethyl acetate. Combined organic extract was washed in turn with water and brine, dried over magnesium sulfate, and evaporated. The residue was chromatographed on silica gel (120 g) eluting with ethyl acetate and hexane (1:1 V/V) to give 2-(3-ethoxycarbonyl-2-propenylamino)benzamide (2.53 g) as a solid.

NMR (CDCl$_3$, δ): 1.25 g (3H, t, J=6 Hz), 4.00 (2H, dd, J=1.5, 4 Hz), 4.20 (2H, q, J=6 Hz), 5.85 (1H, br s), 6.00 (1H, td, J=1.5, 12 Hz), 6.55–6.65 (2H, m), 7.00 (1H, td, J=3.5, 12 Hz), 7.25–7.35 (1H, m), 7.40 (1H, dd, J=1.5, 6.5 Hz)

Preparation 2-2)

To a solution of 2-(3-ethoxycarbonyl-2-propenylamino)benzamide (2.35 g) in methanol (50 ml) was added 10% palladium on carbon (230 mg). The mixture was stirred vigorously under 3 atmospheric pressure of hydrogen. After 2 hours, the catalyst was filtered off, and the solvent was evaporated. The residue was chromatographed on silica gel (40 g). Elution with a mixed solvent of ethyl acetate-hexane (1:1 V/V) gave 2-(3-ethoxycarbonylpropylamino)benzamide (1.95 g).

NMR (CDCl$_3$, δ): 1.25 (3H, t, J=6 Hz), 1.90–2.10 (2H, m), 2.45 (2H, t, J=6 Hz), 3.25 (2H, t, J=6 Hz), 4.15 (2H, q, J=6 Hz), 5.75 (1H, br s), 6.65 (1H, t, J=6 Hz), 6.80 (1H, d, J=7 Hz), 7.30–7.45 (2H, m)

Preparation 2-3)

A mixture of 2-(3-ethoxycarbonylpropylamino)benzamide (1.95 g) and N,N'-carbonyldiimidazole (2.52 g) in dioxane (20 ml) was heated to 150° C. After 30 minutes, the mixture was cooled below 80° C., and diluted with ethanol to give crude crystals. Collected crystals were recrystallized from ethanol to give 1-(3-ethoxycarbonylpropyl)-2,4(1H,3H)-quinazolinedione (1.53 g) as a crystal.

NMR (CDCl$_3$, δ): 1.30 (3H, t, J=6 Hz), 2.00–2.15 (2H, m), 2.50 (2H, t, J=5 Hz), 4.10–4.30 (4H, m), 7.30 (1H, t, J=8 Hz), 7.50 (1H, d, J=8 Hz), 7.25 (1H, dt, J=1.5, 8 Hz), 8.25 (1H, dd, J=1.5, 8 Hz), 8.70 (1H, br s)

Preparation 3

A mixture of 1-(3-carboxypropyl)-2,4(1H,3H)-quinazolinedione (744 mg) and thionyl chloride (1.3 ml) in dry tetrahydrofuran (12 ml) was refluxed for 1 hour, and then evaporated. Obtained residue dissolved in tetrahydrofuran (15 ml) was added to a mixture of N-(2-nitrophenyl)piperazine (683 mg) and triethylamine (607 mg) in chloroform (15 ml) on an ice-bath. After stirring for 1 hour, precipitated materials were collected and dissolved in chloroform, washed in turn with water, saturated sodium bicarbonate and brine, dried over magnesium sulfate, and evaporated to give 1-[4-(4-(2-nitrophenyl)piperazin-1-yl)-4-oxobutyl]-2,4(1H,3H)-quinazolinedione (1.06 g) as a solid.

NMR (CDCl$_3$, δ): 2.00–2.20 (2H, m), 2.55 (2H, t, J=5 Hz), 3.10 (1H, t, J=4 Hz), 3.60–3.70 (2H, m), 3.80–3.90 (2H, m), 4.20 (2H, t, J=6.5 Hz), 7.15 (2H, d, J=6 Hz), 7.30 (1H, dt, J=1.5, 6 Hz), 7.50 (1H, dt, J=1.5, 6 Hz), 7.70–7.85 (3H, m), 8.20 (1H, dd, J=1.5, 6 Hz), 8.65 (1H, br s)

Preparation 4

A mixture of 1-(3-carboxy)propyl-2,4(1H,3H)-quinazolinedione (744 mg) and thionyl chloride (1.30 ml) in dry tetrahydrofuran (10 ml) was refluxed for 1 hour, and then evaporated in vacuo. Obtained residue dissolved in dry tetrahydrofuran (5 ml) was added to a stirred mixture of 4-(4-chlorophenyl)-1,2,3,6-tetrahydropyridine hydro-chloride (719 mg) and triethylamine (911 mg) in chloroform-tetrahydrofuran (10 ml, 1:1 V/V) on an ice-bath. After stirring for 1 hour at the same temperature, the reaction mixture was diluted with chloroform, washed with water, 1N hydrochloric acid, saturated sodium bicarbonate, and brine successively, dried over magnesium sulfate, and evaporated. The residue was chromatographed on silica gel (20 g). Elution with a mixed solvent of chloroform and methanol (50:1 V/V) gave 1-[4-{4-(4-chlorophenyl)-1,2,3,6-tetrahydropyridin-1-yl}-4-oxobutyl]-2,4(1H,3H)-quinazolinedione (1.365 g) as an amorphous.

NMR (CDCl$_3$, δ): 1.95–2.20 (2H, m), 2.40–2.65 (4H, m), 3.70 (1H, t, J=5 Hz), 3.85 (1H, t, J=5 Hz), 4.10–4.30 (4H, m), 5.95–6.15 (1H, m), 7.15–7.25 (5H, m), 7.60–7.80 (2H, m), 8.20 (1H, d, J=8 Hz), 9.05 (1H, br s)

Preparation 5-1)

To a stirred solution of methyl 2-ethoxycarbonylamino-4-nitrobenzoate (4.00 g) in dry dimethylformamide (40 ml) was added sodium hydride (715 mg, 60% oil suspension) in several portions on an ice-bath. After stirring for 1 hour, 1-bromo-4-chlorobutane (2.81 g) was added thereto, and the resulted mixture was stirred for 18 hours at room temperature. The reaction mixture was poured into ice-water, and extracted with ethyl acetate. The extract was washed in turn with water and brine, dried over magnesium sulfate, and evaporated. The residue was chromatographed on silica gel (180 g). Elution with a mixed solvent of hexane and ethyl acetate (3:1 V/V) gave methyl 2-[N-(4-chlorobutyl)-N-ethoxycarbonylamino]-4-nitrobenzoate (2.30 g) as an oil.

NMR (CDCl$_3$, δ): 1.05–1.20 (3H, m), 1.70–1.95 (4H, m), 3.30–3.60 (3H, m), 3.90 (3H, s), 4.00–4.40 (3H, m), 8.05–8.25 (3H, m)

Preparation 5-2)

A mixture of methyl 2-[N-(4-chlorobutyl)-N-ethoxycarbonylamino]-4-nitrobenzoate (2.20 g), 4-phenyl-1,2,3,6-tetrahydropyridine hydrochloride (1.32 g), sodium iodide (921 mg), and potassium carbonate (1.69 g) in dry dimethylformamide (30 ml) was stirred at 80° C. for 16 hours. The reaction mixture was poured into ice-water, extracted with ethyl acetate. Combined organic extract was washed in turn with water and brine, dried over magnesium sulfate, and evaporated. The crude residue was chromatographed on silica gel (40 g), eluting with a mixed solvent of chloroform and methanol (50:1 V/V) to give methyl 2-[N-{4-(4-phenyl-1,2,3,6-tetrahydropyridin-1-yl)butyl}-N-ethoxycarbonylamino]-4-nitrobenzoate (1.58 g).

NMR (CDCl$_3$, δ): 1.10 (2H, t, J=6 Hz), 1.20–1.45 (1H, m), 1.60–1.80 (4H, m), 2.50–2.65 (4H, m), 2.70–2.80 (2H, m), 3.15–3.25 (2H, m), 3.50–3.90 (2H, m), 3.90 (3H, s), 4.00–4.35 (2H, m), 6.00–6.10 (1H, m), 7.25–7.40 (5H, m), 8.00–8.20 (3H, m)

Preparation 5-3)

To a stirred solution of methyl 2-[N-{4-(4-phenyl-1,2,3,6-tetrahydropyridin-1-yl)butyl}-N-ethoxycarbonylamino]-4-nitrobenzoate (1.58 g) in methanol (16 ml) was added 2N potassium hydroxide (5.0 ml). After stirring for 2 hours at 50° C., methanol was evaporated in vacuo. The residue was diluted with water, acidified with 3N hydrochloric acid, extracted with chloroform. The extract was washed with brine, dried over magnesium sulfate, and evaporated. Crude 2-[N-{4-(4-phenyl-1,2,3,6-tetrahydropyridin-1-yl)butyl}-N-ethoxycarbonylamino]-4-nitrobenzoic acid (1.57 g) was obtained as an amorphous.

NMR (CDCl$_3$, δ): 0.90–1.10 (3H, m), 1.55–1.80 (2H, m), 1.90–2.05 (2H, m), 2.80–3.00 (2H, m), 3.00–3.15 (2H, m), 3.30–3.50 (2H, m), 3.65–4.10 (6H, m), 6.00 (1H, br s), 7.25–7.40 (5H, m), 7.95–8.20 (3H, m)

Preparation 5-4)

A mixture of 2-[N-{4-(4-phenyl-1,2,3,6-tetrahydropyridin-1-yl)butyl}-N-ethoxycarbonylamino]-4-nitrobenzoic acid (1.53 g), N,N'-disuccinimidoyl carbonate (924 mg) and pyridine (285 mg) in dry acetonitrile (20 ml) was stirred for 3 hours at room temperature. Then, to the mixture was added 28% ammonium hydroxide (1.4 ml) on an ice-bath. After 1 hour, the reaction mixture was diluted with water, and extracted with chloroform. The extract was washed with brine, dried over magnesium sulfate, and evaporated. The residue was chromatographed on silica gel (30 g). Elution with a mixed solvent of chloroform and methanol (50:1 V/V) gave 2-[N-{4-(4-phenyl-1,2,3,6-tetrahydropyridin-1-yl)butyl}-N-ethoxycarbonylamino]-4-nitrobenzamide (600 mg) as caramel.

NMR (CDCl$_3$, δ): 1.30 (3H, t, J=6 Hz), 1.50–1.75 (4H, m), 2.45–2.65 (4H, m), 2.70–2.80 (2H, m), 3.15–3.25 (2H, m), 3.60–3.75 (2H, m), 4.20 (2H, q, J=6 Hz), 5.90–6.10 (2H, m), 7.20–7.40 (5H, m), 7.80 (1H, d, J=7 Hz), 8.10 (1H, d, J=1.5 Hz), 8.25 (1H, dd, J=1.5, 7 Hz)

Preparation 6

To a stirred suspension of 1-[4-hydroxybutyl)-2,4(1H,3H)-quinazolinedione (778 mg) in chloroform-tetrahydrofuran (40 ml, 1:1 V/V) was added methanesulfonyl chloride (0.57 ml), and triethylamine (1.85 ml) on an ice-bath. After stirring for 18 hours at room temperature, the reaction mixture was heated at 50° C. for 30 hours with stirring. After evaporation of the solvents the residue was diluted with ethyl acetate. The mixture was washed in turn with water and brine, dried over magnesium sulfate, and evaporated. 1-(4-Methanesulfonyloxybutyl)-2,4(1H,3H)-quinazolinedione (675 mg) as a crystal was obtained by recrystallization from methanol.

NMR (CDCl$_3$, δ): 1.85–2.00 (4H, m), 3.00 (3H, s), 4.15–4.25 (2H, m), 4.30–4.40 (2H, m), 7.20–7.35 (2H, m), 7.70 (1H, dt, J=1.5, 6 Hz), 8.25 (1H, dd, J=1.5, 6 Hz), 8.70 (1H, br s)

Preparation 7-1)

Methyl-6-chloro-2-[N-(4-chlorobutyl)-N-ethoxycarbonylamino]benzoate was obtained in 90.7% yield in substantially the same manner as that of Preparation 5-1).

NMR (CDCl$_3$, δ): 1.10–1.25 (3H, m), 1.65–1.85 (4H, m), 3.20–3.50 (1H, m), 3.55 (2H, t, J=6 Hz), 3.65–3.85 (1H, m), 3.90 (3H, s), 4.05–4.20 (2H, m), 7.05–7.15 (1H, m), 7.35–7.45 (2H, m)

Preparation 7-2)

Methyl 6-chloro-2-[N-ethoxycarbonyl-N-{4-(4-phenyl-1,2,3,6-tetrahyxropyridin-1-yl)butyl}amino]benzoate was obtained in 78.2% yield in substantially the same manner as that of Preparation 5-2).

NMR (CDCl$_3$, δ): 1.05–1.30 (3H, m), 1.55–1.70 (4H, m), 2.40–2.75 (6H, m), 3.10–3.20 (2H, m), 3.20–3.50 (1H, m), 3.70–3.90 (1H, m), 3.90 (3H, s), 4.00–4.20 (2H, m), 6.05–6.10 (1H, m), 7.10–7.60 (8H, m)

Preparation 7-3)

6-Chloro-2-[N-ethoxycarbonyl-N-{4-(4-phenyl-1,2,3,6-tetrahydropyridin-1-yl)butyl)amino]benzoic acid was obtained in 96.1% yield in substantially the same manner as that of Preparation 5-3).

IR (Nujol): 1680, 1600, 1580 cm$^{-1}$

Preparation 7-4)

6-Chloro-2-[N-ethoxycarbonyl-N-{4-(4-phenyl-1,2,3,6-tetrahydropyridin-1-yl)butyl}amino]benzamide was obtained in 21.0% yield in substantially the same manner as that of Preparation 5-4).

NMR (CDCl$_3$, δ): 1.05–1.45 (3H, m), 1.50–1.90 (4H, m), 2.50–2.95 (4H, m), 3.20–3.40 (1H, m), 3.60–3.80 (1H, m), 4.00–4.30 (2H, m), 6.00–6.10 (1H, m), 7.05–7.50 (8H, m)

Preparation 8-1)
Methyl 2-[N-(4-chlorobutyl)-N-ethoxycarbonylamino-6-nitrobenzoate was obtained in substantially the same manner as that of Preparation 5-1).

NMR (CDCl$_3$, δ): 1.00–1.30 (3H, m), 1.65–1.85 (4H, m), 3.50–3.60 (2H, m), 3.90 (3H, s), 4.05–4.20 (2H, m), 7.55 (1H, d, J=7 Hz), 7.65 (1H, t, J=7 Hz), 8.15 (1H, dd, J=1, 7 Hz) Preparation 8-2)

Methyl 2-[N-{4-(4-phenyl-1,2,3,6-tetrahydropyridin-1-yl)butyl}-N-ethoxycarbonylamino]-6-nitrobenzoate was obtained in substantially the same manner as that of Preparation 5-2).

NMR (CDCl$_3$, δ): 1.05–1.25 (3H, m), 1.55–1.75 (4H, m), 2.50–2.65 (4H, m), 2.75 (2H, t, J=4 Hz), 3.20 (2H, d, J=3 Hz), 3.90 (3H, s), 4.00–4.20 (2H, m), 6.00–6.10 (1H, m), 7.25–7.40 (5H, m), 7.55–7.65 (2H, m), 8.10 (1H, d, J=7 Hz)

Preparation 8-3)
2-[N-{4-(4-Phenyl-1,2,3,6-tetrahydropyridin-1-yl)butyl}-N-ethoxycarbonylamino]-6-nitrobenzoic acid was obtained in substantially the same manner as that of Preparation 5-3).

NMR (CDCl$_3$, δ): 1.00–1.25 (3H, m), 1.55–1.80 (2H, m), 1.90–2.10 (2H, m), 2.70–3.20 (3H, m), 3.40–4.20 (9H, m), 6.00 (1H, s), 7.25–7.50 (7H, m), 8.00 (1H, t, J=7 Hz)

Preparation 8-4)
A mixture of 2-[N-{4-(4-phenyl-1,2,3,6-tetrahydropyridin-1-yl)butyl}-N-ethoxycarbonylamino]-6nitrobenzoic acid (680 mg) and phosphorus tribromide (0.7 ml) in methylene dichloride (30 ml) was refluxed for 3 hours. Excess of phosphorus tribromide was quenched with ethanol (2 ml) on an ice-bath. Then appeared crystalline materials were collected, and washed with ethanol to give 1-[4-(4-phenyl-1,2,3,6-tetrahydropyridin-1-yl)butyl]-5-nitro-1,2-dihydro-4H-3,1-benzoxazine-2,4-dione hydrobromide 414 mg).

NMR (DMSO-d$_6$, δ): 1.65–1.95 (4H, m), 2.75–2.90 (2H, m), 3.20–3.40 (3H, m), 3.10–3.90 (2H, m), 4.00–4.20 (3H, m), 6.15–6.25 (1H, m), 7.35–7.55 (5H, m), 7.70 (1H, d, J=6 Hz), 7.80 (1H, d, J=6 Hz), 8.05 (1H, t, J=6 Hz)

Preparation 8-5)
To a suspension of 1-[4-(4-phenyl-1,2,3,6-tetrahydropyridin-1-yl)butyl]-5-nitro-1,2-dihydro-4H-3,1-benzoxazine-2,4-dione hydrobromide (410 mg) in dimethylformamide (4 ml) was added 28% ammonium hydroxide (1 ml) on an ice-bath, and the mixture was stirred for 1 hour at room temperature. The mixture was poured into ice-water, extracted with ethyl acetate, and the extracts were washed with water and brine. After dryness with magnesium sulfate and evaporation of the solvent, 2-[4-(4-phenyl-1,2,3,6-tetrahydropyridin-1-yl)butylamino]-6nitrobenzamide was obtained as an amorphous (300 mg).

NMR (CDCl$_3$, δ): 1.60–1.80 (4H, m), 2.40–2.60 (4H, m), 2.70 (2H, t, J=5 Hz), 3.10–3.25 (4H, m), 5.10–5.20 (1H, m), 6.00–6.10 (3H, m), 6.90 (1H, dd, J=1.5, 7 Hz), 7.20–7.40 (7H, m)

The following compounds were obtained in substantially the same manner as that of Preparation 5-1).

Preparation 9-1)
Ethyl 2-[N-(4-chlorobutyl)-N-ethoxycarbonylamino]-5-ethoxybenzoate NMR (CDCl$_3$, δ): 1.10 (2H, t, J=6 Hz), 1.25 (1H, t, J=6 Hz), 1.35 (3H, t, J=6 Hz), 1.45 (3H, t, J=6 Hz), 1.60–1.90 (4H, m), 3.25–3.40 (1H, m), 3.55 (2H, t, J=5 Hz), 3.80–4.25 (5H, m), 4.30 (2H, q, J=6 Hz), 7.05 (1H, dd, J=2, 7 Hz), 7.10 (1H, d, J=7 Hz), 7.50 (1H, d, J=2 Hz)

Preparation 9-2)
Methyl 2-[N-(4-chlorobutyl)-N-ethoxycarbonylamino]-5-methoxybenzoate NMR (CDCl$_3$, δ): 1.10 (2H, t, J=6 Hz), 1.35 (1H, dd, J=6, 12 Hz), 1.70–1.90 (4H, m), 3.30–3.45 (1H, m), 3.55 (2H, t, J=5 Hz), 3.90 (3H×2, s), 3.90–4.40 (3H, m), 7.00–7.20 (2H, m), 7.50 (1H, d, J=2 Hz)

Preparation 9-3)
Methyl 2-[N-(4-chlorobutyl)-N-ethoxycarbonylamino]-3-chlorobenzoate NMR (CDCl$_3$, δ): 1.10 (3H, t, J=6 Hz), 1.60–1.85 (4H, m), 3.35–3.70 (4H, m), 3.90 (3H, s), 4.10 (2H, q, J=6 Hz), 4.20–4.40 (1H, m), 7.35 (1H, t, J=7 Hz), 7.65 (1H, dd, J=1.5, 7 Hz), 7.85 (1H, dd, J=1.5, 7 Hz)

Preparation 9-4)
Methyl 2-[N-(4-chlorobutyl)-N-ethoxycarbonylamino]-4-methoxybenzoate NMR (CDCl$_3$, δ): 1.10 (2H, t, J=6 Hz), 1.20–1.40 (1H, m), 3.35–3.50 (1H, m), 3.55 (2H, t, J=5 Hz), 3.85 (3H, s), 3.90 (3H, s), 3.80–4.25 (3H, m), 6.70–6.80 (1H, m), 6.85 (1H, dd, J=2, 8 Hz), 8.00 (1H, d, J=8 Hz)

Preparation 9-5)
Methyl 2-[N-(4-chlorobutyl)-N-ethoxycarbonylamino]-4,5-dimethoxybenzoate NMR (CDCl$_3$, δ): 1.10 (2H, t, J=6 Hz), 1.30–1.40 (1H, m), 1.65–1.95 (4H, m), 3.30–3.60 (3H, m), 3.85 (3H, s), 3.90 (3H x 2, s), 3.95–4.35 (3H, m), 6.65 (1H, s), 7.50 (1H, s)

Preparation 9-6)
Methyl 2-[N-[4-chlorobutyl)-N-ethoxycarbonylamino]-5-nitrobenzoate NMR (CDCl$_3$, δ): 1.00–1.20 (3H, m), 1.70–1.90 (4H, m), 3.50–3.60 (2H, m), 3.70–3.80 (2H, m), 3.90 (3H, s), 4.00–4.20 (2H, m), 7.45 (1H, d, J=8 Hz), 8.40 (1H, dd, J=2, 8 Hz), 8.80 (1H, br s)

Preparation 9-7)
Methyl 2-[N-(4-chlorobutyl)-N-ethoxycarbonylamino]-6-fluorobenzoate NMR (CDCl$_3$, δ): 1.05–1.30 (3H, m), 1.65–1.90 (4H, m), 3.40–3.70 (4H, m), 3.90 (3H, s), 4.00–4.20 (2H, m), 7.05 (1H, d, J=7 Hz), 7.15 (1H, d, J=7 Hz), 7.45 (1H, dt, J=4, 7 Hz)

Preparation 9-8)
Methyl 2-[N-(4-chlorobutyl)-N-ethoxycarbonylamino]-6-methoxybenzoate NMR (CDCl$_3$, δ): 1.10–1.25 (3H, m), 1.65–1.85 (4H, m), 3.55 (2H, t, J=5 Hz), 3.90 (6H, s), 4.00–4.20 (2H, m), 6.80 (1H, d, J=7 Hz), 6.90 (1H, d, J=7 Hz), 7.40 (1H, t, J=7 Hz)

Preparation 9-9)
Methyl 2-[N-(4-chlorobutyl)-N-ethoxycarbonylamino]-6-methylbenzoate NMR (CDCl$_3$, δ): 1.10–1.30 (3H, m), 1.60–1.90 (4H, m), 2.40 (3H, s), 3.20–3.50 (1H, m), 3.55 (2H, t, J=5 Hz), 3.70–4.00 (1H, m), 3.90 (3H, s), 4.00–4.20 (2H, m), 7.00 (1H, d, J=7 Hz), 7.20 (1H, d, J=7 Hz), 7.35 (1H, t, J=7 Hz)

The following compounds were obtained in substantially the same manner as that of Preparation 5-2).

Preparation 10-1)
Ethyl 2-[N-{4-(4-phenyl-1,2,3,6-tetrahydropyridin-1-yl)butyl}-N-ethoxycarbonylamino]-5-ethoxybenzoate NMR (CDCl$_3$, δ): 1.10 (3H, t, J=6 Hz), 1.35 (3H, t, J=6 Hz), 1.45 (3H, t, J=6 Hz), 1.50–1.70 (4H, m), 2.45–2.80 (6H, m), 3.15–3.40 (3H, m), 3.85–4.15 (5H, m), 4.30 (2H, q, J=6 Hz), 6.00–6.10 (1H, m), 7.00 ( 1H, dd, J=2, 8 Hz), 7.10 (1H, d, J=8 Hz), 7.25–7.40 (5H, m), 7.45 (1H, d, J=2 Hz)

Preparation 10-2)

Methyl 2-[N-{4-(4-phenyl-1,2,3,6-tetrahydropyridin-1-yl)butyl}-N-ethoxycarbonylamino]-5-methoxybenzoate NMR (CDCl₃, δ): 1.10 (3H, t, J=6 Hz), 1.50–1.70 (4H, m), 2.45–2.60 (4H, m), 2.65–2.75 (2H, m), 3.10–3.20 (2H, m), 3.25–3.40 (1H, m), 3.80 (3H×2, s), 3.80–4.35 (3H, m), 6.00–6.10 (1H, m), 7.00–7.50 (8H, m)

Preparation 10-3)

Methyl 2-[N-{4-(4-phenyl-1,2,3,6-tetrahydropyridin-1-yl)butyl)-N-ethoxycarbonylamino]-3-chlorobenzoate NMR (CDCl₃, δ): 1.10 (2H, t, J=6 Hz), 1.35 (1H, m), 1.50–1.65 (4H, m), 2.40–2.70 (6H, m), 3.10–3.20 (2H, m), 3.35–3.80 (2H, m), 3.90 (3H, s), 4.10 (4/3H, q, J=6 Hz), 4.20–4.40 (2/3H, m), 6.00–6.10 (1H, m), 7.20–7.40 (6H, m), 7.65 (1H, dd, J=1.5, 7 Hz), 7.85 (1H, dd, J=1.5, 7 Hz)

Preparation 10-4)

Methyl 2-[N-{4-(4-phenyl-1,2,3,6-tetrahydropyridin-1-yl)butyl}-N-ethoxycarbonylamino]-4-methoxybenzoate NMR (CDCl₃, δ): 1.10 (12/5H, t, J=6 Hz), 1.35 (3/5H, t, J=6 Hz), 1.60–1.75 (4H, m), 2.50–2.70 (4H, m), 2.70–2.90 (2H, m), 3.20–3.30 (2H, m), 3.30–3.55 (1H, m), 3.85 (3H, s), 3.90 (3H, s), 3.80–4.30 (3H, m), 6.05 (1H, br s), 6.75 (1H, d, J=2 Hz), 6.85 (1H, dd, J=2, 8 Hz), 7.25–7.40 (5H, m), 8.00 (1H, d, J=8 Hz)

Preparation 10-5)

Methyl 2-[N-{4-(4-phenyl-1,2,3,6-tetrahydropyridin-1-yl)butyl}-N-ethoxycarbonylamino]-4,5-dimethoxybenzoate NMR (CDCl₃, δ): 1.10 (2H, t, J=5 Hz), 1.30–1.40 (1H, m), 1.55–1.75 (4H, m), 2.45–2.70 (4H, m), 2.70–2.80 (2H, m), 3.15–3.45 (3H, m), 3.85 (3H, s), 3.90 (3H×2, s), 3.95–4.35 (3H, m), 6.05 (1H, br s), 6.70 (1H, s), 7.25–7.40 (5H, m), 7.50 (1H, s)

Preparation 10-6)

Methyl 2-[N-{4-(4-phenyl-1,2,3,6-tetrahydropyridin-1-yl)butyl-N-ethoxycarbonylamino]-5-nitrobenzoate NMR (CDCl₃, δ): 1.00–1.50 (3H, m), 1.60–1.80 (4H, m), 2.50–2.70 (4H, m), 2.75–2.90 (2H, m), 3.20–3.30 (2H, m), 3.60–3.90 (2H, m), 3.90 (3H, s), 4.00–4.30 (2H, m), 6.00–6.10 (1H, m), 7.25–7.50 (6H, m), 8.40 (1H, dd, J=2, 8 Hz), 8.80 (1H, br s)

Preparation 10-7)

Methyl 2-[N-{4-(4-phenyl-1,2,3,6-tetrahydropyridin-1-yl)butyl}-N-ethoxycarbonylamino]-6-fluorobenzoate NMR (CDCl₃, δ): 1.05–1.25 (3H, m), 1.55–1.80 (4H, m), 2.60–2.75 (4H, m), 2.80–2.95 (2H, m), 3.25–3.40 (2H, m), 3.40–3.80 (2H, m), 3.90 (3H, s), 4.00–4.20 (2H, m), 6.00–6.10 (1H, m), 7.00–7.15 (2H, m), 7.25–7.50 (6H, m)

Preparation 10-8)

Methyl 2-[N-{4-(4-phenyl-1,2,3,6-tetrahydropyridin-1-yl)butyl}-N-ethoxycarbonylamino]-6-methoxybenzoate NMR (CDCl₃, δ): 1.10–1.25 (3H, m), 1.55–1.75 (4H, m), 2.50–2.70 (4H, m), 3.80–3.90 (2H, m), 3.75–3.85 (2H, m), 3.90 (6H, s), 4.00–4.20 (2H, m), 6.00–6.10 (1H, m), 6.80 (1H, d, J=7 Hz), 6.90 (1H, d, J=7 Hz), 7.25–7.45 (6H, m)

Preparation 10-9)

Methyl 2-[N-{4-(4-phenyl-1,2,3,6-tetrahydropyridin-1-yl)butyl}-N-ethoxycarbonylamino]-6-methylbenzoate NMR (CDCl₃, δ): 1.10–1.25 (3H, m), 1.55–1.80 (4H, m), 2.40 (3H, s), 2.55–2.75 (4H, m), 2.75–2.95 (2H, m), 3.20–3.45 (2H, m), 3.90 (3H, s), 4.00–4.20 (2H, m), 6.00–6.10 (1H, m), 7.05 (1H, d, J=7 Hz), 7.15–7.40 (7H, m)

The following compounds were obtained in substantially the same manner as that of Preparation 5-3).

Preparation 11-1)

2-[N-{4-(4-Phenyl-1,2,3,6-tetrahydropyridin-1-yl)butyl}-N-ethoxycarbonylamino]-5-ethoxybenzoic acid NMR (CDCl₃, δ): 1.40 (3H, t, J=6 Hz), 1.50–1.75 (2H, m), 1.75–1.95 (2H, m), 2.75–3.00 (4H, m), 3.20–3.70 (6H, m), 3.85–4.10 (4H, m), 6.00 (1H, br s), 6.90 (1H, dd, J=2, 7.5 Hz), 6.95 (1H, d, J=7.5 Hz), 7.20–7.50 (6H, m)

Preparation 11-2)

2-[N-{4-(4-Phenyl-1,2,3,6-tetrahydropyridin-1-yl)butyl}-N-ethoxycarbonylamino]-5-methoxybenzoic acid NMR (CDCl₃, δ): 1.00 (3H, t, J=6 Hz), 1.50–1.65 (2H, m), 1.70–2.05 (2H, m), 2.80–3.10 (4H, m), 3.30–3.40 (2H, m), 3.55–3.70 (2H, m), 3.80 (5H, br s), 4.00 (2H, q, J=6 Hz), 6.00 (1H, br s), 6.95 (1H, dd, J=2, 8 Hz), 7.00 (1H, d, J=8 Hz), 7.20–7.40 (5H, m), 7.45 (1H, d, J=2 Hz)

Preparation 11-3)

2-[N-{4-(4-Phenyl-1,2,3,6-tetrahydropyridin-1-yl)butyl)-N-ethoxycarbonylamino]-3-chlorobenzoic acid Preparation 11-4)

2-[N-{4-(4-Phenyl-1,2,3,6-tetrahydropyridin-1-yl)butyl}-N-ethoxycarbonylamino]-4-methoxybenzoic acid NMR (CDCl₃, δ): 1.05 (3H, t, J=6 Hz), 1.50–1.70 (2H, m), 1.85–2.05 (2H, m), 2.80–2.90 (2H, m), 2.95–3.10 (2H, m), 3.30–3.40 (2H, m), 3.55–3.80 (4H, m), 3.85 (3H, s), 4.00 (2H, q, J=6 Hz), 6.65 (1H, d, J=1.5 Hz), 6.80 (1H, dd, J=1.5, 7.5 Hz), 7.25–7.40 (5H, m), 8.00 (1H, d, J=7.5 Hz)

Preparation 11-5)

2-[N-{4-(4-Phenyl-1,2,3,6-tetrahydropyridin-1-yl)butyl}-N-ethoxycarbonylamino]-4,5-dimethoxybenzoic acid NMR (CDCl₃, δ): 1.05 (3H, t, J=6 Hz), 1.50–1.70 (2H, m), 1.90–2.10 (2H, m), 2.85–3.20 (4H, m), 3.30–3.50 (2H, m), 3.60–3.75 (2H, m), 3.90 (3H×2, s), 3.80–4.10 (4H, m), 6.00 (1H, br s), 6.60 (1H, s), 7.25–7.40 (5H, m), 7.55 (1H, s)

Preparation 11-6)

2-[N-{4-(4-Phenyl-1,2,3,6-tetrahydropyridin-1-yl)butyl}-N-ethoxycarbonylamino]-5-nitrobenzoic acid NMR (CDCl₃, δ): 1.10–1.20 (3H, m), 1.50–1.70 (2H, m), 2.00–2.20 (2H, m), 2.85–3.00 (2H, m), 3.10–3.20 (2H, m), 3.40–3.60 (2H, m), 3.70–4.00 (4H, m), 4.00–4.15 (2H, m), 6.00 (1H, br s), 7.25–7.40 (6H, m), 8.20–8.30 (1H, m), 8.65–8.75 (1H, m)

Preparation 11-7)

2-[N-{4-(4-Phenyl-1,2,3,6-tetrahydropyridn-1-yl)butyl} -N-ethoxycarbonylamino]-6-fluorobenzoic acid NMR (CDCl₃, δ): 1.05–1.30 (3H, m), 1.55–1.75 (2H, m), 1.90–2.10 (2H, m), 2.80–3.00 (2H, m), 3.10 (2H, t, J=6 Hz), 3.30–3.50 (2H, m), 3.60–3.90 (4H, m), 4.00–4.20 (2H, m), 6.00 (1H, br s), 6.90–7.10 (2H, m), 7.20–7.40 (2H, m)

Preparation 11-8)

2-[N-{4-(4-Phenyl-1,2,3,6-tetrahydropyridin-1-yl)butyl)-N-ethoxycarbonylamino]-6-methoxybenzoic acid NMR (CDCl$_3$, δ): 1.00–1.20 (3H, m), 1.55–1.75 (2H, m), 1.85–2.10 (2H, m), 3.80–3.95 (2H, m), 3.05 (2H, t, J=6 Hz), 3.35–3.50 (2H, m), 3.60–3.80 (7H, m), 4.00–4.15 (2H, m), 5.80 (1H, br s), 6.00 (1H, br s), 6.70 (1H, d, J=6 Hz), 6.85 (1H, d, J=6 Hz), 7.20–7.40 (6H, m)

Preparation 11-9)
2-[N-{4-(4-Phenyl-1,2,3,6-tetrahydropyridin-1-yl)butyl}-N-ethoxycarbonylamino]-6-methylbenzoic acid NMR (CDCl$_3$, δ): 1.00–1.30 (3H, m), 1.30–1.80 (2H, m), 1.85–2.40 (2H, m), 2.45 (3H, s), 2.60–2.85 (1H, m), 2.90–3.40 (5H, m), 3.50–3.80 (2H, m), 4.00–4.35 (4H, m), 6.10 (1H, br s), 7.00 (1H, d, J=7 Hz), 7.15–7.40 (7H, m)

The following compounds were obtained in substantially the same manner as that of Preparation 5-4).

Preparation 12-1)
2-[N-{4-(4-Phenyl-1,2,3,6-tetrahydropyridin-1-yl)butyl)-N-ethoxycarbonylamino]-5-ethoxybenzamide Preparation 12-2)
2-[N-{4-(4-Phenyl-1,2,3,6-tetrahydropyridin-1-yl)butyl} -N-ethoxycarbonylamino]-5-methoxybenzamide NMR (CDCl$_3$, δ): 1.25 (3H, t, J=6 Hz), 1.50–1.65 (4H, m), 2.45–2.65 (4H, m), 2.70–2.80 (2H, m), 3.20 (2H, m), 3.60 (2H, br s), 3.80 (3H, s), 4.20 (2H, q, J=6 Hz), 6.00–6.10 (1H, m), 7.00 (1H, dd, J=2, 8 Hz), 7.10 (1H, d, J=8 Hz), 7.20–7.40 (6H, m)

Preparation 12-3)
2-[N-{4-(4-Phenyl-1,2,3,6-tetrahydropyridin-1-yl)butyl}-N-ethoxycarbonylamino]-3-chlorobenzamide NMR (CDCl$_3$, δ): 1.20 (3/2H, t, J=6 Hz), 1.35 (3/2H, t, J=6 Hz), 1.50–1.75 (4H, m), 2.40–2.80 (6H, m), 3.15–3.50 (3H, m), 3.70–4.00 (1H, m), 4.10–4.40 (2H, m), 5.85 (1/2H, br s), 6.00–6.20 (2H, m), 6.80 (1H, br s), 7.20–7.40 (6H, m), 7.50–7.65 (2H, m)

Preparation 12-4)
2-[N-{4-(4-Phenyl-1,2,3,6-tetrahydropyridin-1-yl)butyl}-N-ethoxycarbonylamino]-4-methoxybenzamide NMR CDCl$_3$, δ): 1.25 (3H, t, J=6 Hz), 1.55–1.70 (4H, m), 2.45–2.70 (4H, m), 2.75 (2H, m), 3.15–3.25 (2H, m), 3.50–3.75 (2H, m), 3.85 (3H, s), 4.20 (2H, q, J=6 Hz), 6.00–6.10 (1H, m), 6.70 (1H, d, J=2 Hz), 6.90 (1H, dd, J=2, 7 Hz), 7.20–7.40 (6H, m), 7.70 (1 or 2H, d, J=7 Hz)

Preparation 12-5)
2-[N-{4-(4-Phenyl-1,2,3,6-tetrahydropyridin-1-yl)butyl}-N-ethoxycarbonylamino]-4,5-dimethoxybenzamide NMR (CDCl$_3$, δ): 1.35 (3H, t, J=6 Hz), 1.55–1.65 (4H, m), 2.40–2.50 (2H, m), 3.55–3.65 (2H, m), 3.90 (3H, s), 3.95 (3H, s), 4.20 (2H, q, J=6 Hz), 5.75–5.90 (3/5H, br s), 6.00–6.10 (1H, m), 6.60 (1H, s), 7.25–7.40 (8H, m)

Preparation 12-6)
2-[N-{4-(4-Phenyl-1,2,3,6-tetrahydropyridin-1-yl)butyl}-N-ethoxycarbonylamino]-5-nitrobenzamide NMR (CDCl$_3$, δ): 1.20–1.35 (3H, m), 1.55–1.90 (4H, m), 2.50–2.70 (4H, m), 2.70–2.90 (2H, m), 3.20–3.35 (2H, m), 4.10–4.30 (2H, m), 6.05 (1H, br s), 7.20–7.45 (6H, m), 8.30 (1H, d, J=2 Hz), 9.00 (1H, d, J=2 Hz)

The following Compounds were obtained in substantially the same manner as that of Preparations 8-4) and 8-5).

Preparation 13-1)
2-[N-{4-(4-Phenyl-1,2,3,6-tetrahydropyridin-1-yl)butyl}amino]-6-fluorobenzamide NMR (CDCl$_3$, δ): 1.65–1.85 (4H, m), 2.50–2.70 (4H, m), 2.80 (2H, t, J=4 Hz), 6.05–6.10 (1H, m), 6.30 (1H, ddd, J=1, 8, 10 Hz), 6.50 (1H, d, J=7 Hz), 7.20–7.45 (6H, m), 8.55 (1H, br s)

Preparation 13-2)
2-[N-{4-(4-Phenyl-1,2,3,6-tetrahydropyridin-1-yl)butyl}amino]-6-methoxybenzamide NMR CDCl$_3$, δ): 1.70–1.85 (4H, m), 2.55–2.70 (4H, m), 2.85 (2H, t, J=5 Hz), 3.15–3.35 (4H, m), 3.90 (3H, s), 5.50 (1H, br s), 6.00–6.10 (1H, m), 6.20 (1H, d, J=7 Hz), 6.35 (1H, d, J=7 Hz), 7.15–7.40 (6H, m), 7.80 (1H, br s)

Preparation 13-3)
2-[N-{4-(4-Phenyl-1,2,3,6-tetrahydropyridin-1-yl)butyl}amino]-6-methylbenzamide NMR (CDCl$_3$, δ): 1.60–1.80 (4H, m), 2.40 (3H, s), 2.50–2.70 (4H, m), 2.70–2.80 (2H, m), 3.10–3.25 (4H, m), 4.90 (1H, br s), 5.75–5.95 (2H, m), 6.00–6.10 (1H, m), 6.50 (2H, d, J=7 Hz), 7.10 (1H, t, J=7 Hz), 7.25–7.40 (6H, m)

The following compounds were obtained in substantially the same manner as that of Preparation 2-1).

Preparation 14-1)
2-(3-Ethoxycarbonyl-2-propenylamino)-5-methoxybenzamide

NMR (CDCl$_3$, δ): 1.30 (3H, t, J=5 Hz), 3.80 (3H, s), 3.95–4.05 (2H, m), 4.20 (2H, q, J=5 Hz), 5.90 (1 or 2H, br s), 6.05 (1H, td, J=1.5, 12 Hz), 6.50–6.60 (1H, m), 6.95–7.10 (3H, m)

Preparation 14-2)
2-(3-Ethoxycarbonyl-2-propenylamino)-4-chlorobenzamide

NMR (CDCl$_3$, δ): 1.30 (3H, t, J=6 Hz), 4.00 (2H, dd, J=1.5, 5 Hz), 4.20 (2H, q, J=6 Hz), 5.90 (2H, br s), 6.00 (1H, td, J=1, 12 Hz), 6.55–6.65 (2H, m), 7.00 (1H, td, J=3, 12 Hz), 7.35 (1H, d, J=7 Hz)

The following compounds were obtained in substantially the same manner as that of Preparation 2-2).

Preparation 15-1)
2-3-Ethoxycarbonylpropylamino)-5-methoxybenzamide

NMR (CDCl$_3$, δ): 1.25 (3H, t, J=6 Hz), 1.90–2.05 (2H, m), 2.40 (2H, t, J=6 Hz), 3.20 (2H, t, J=6 Hz), 3.75 (3H, s), 4.15 (2H, q, J=6 Hz), 5.90 (2H, br s), 6.65–6.75 (1H, m), 6.95–7.05 (2H, m)

Preparation 15-2)
2-(3-Ethoxycarbonylpropylamino)-4-chlorobenzamide

NMR (CDCl$_3$, δ): 1.25 (3H, t, J=6 Hz), 1.90–2.10 (2H, m), 2.45 (2H, t, J=5 Hz), 3.20 (2H, t, J=5 Hz), 4.15 (2H, q, J=6 Hz), 5.80 (2H, br s), 6.55 (1H, dd, J=1.5, 8 Hz), 6.70 (1H, d, J=1.5 Hz), 7.30 (1H, d, J=8 Hz)

The following compounds were obtained in substantially the same manner as that of Preparation 2-3).

Preparation 16-1)
3-Ethoxycarbonylpropyl)-6-methoxy-2,4(1H,3H)-quinazolinedione

NMR (CDCl$_3$, δ): 1.30 (3H, t, J=6 Hz), 1.95–2.10 (2H, m), 2.50 (2H, t, J=6 Hz), 3.90 (3H, s), 4.10–4.25 (4H, m), 7.35 (1H, dd, J=2, 8 Hz), 7.45 (1H, d, J=8 Hz), 7.65 (1H, d, J=2 Hz), 8.90 (1H, br s)

Preparation 16-2)
3-Ethoxycarbonylpropyl)-7-chloro-2,4(1H,3H)-quinazolinedione

NMR (CDCl$_3$, δ): 1.30 (3H, t, J=6 Hz), 1.95–2.10 (2H, m), 2.50 (2H, t, J=5 Hz), 4.10–4.30 (4H, m), 7.25

(1H, dd, J=1.5, 7 Hz), 7.50 (1H, d, J=1.5 Hz), 8.15 (1H, d, J=7 Hz), 8.80 (1H, br s)

The following compounds were obtained in substantially the same manner as that of Preparation 1-3).

Preparation 17-1)

1-(3-Carboxypropyl)-6-methoxy-2,4(1H,3H)-quinazolinedione

NMR (DMSO-d6, δ): 1.70–1.90 (2H, m), 2.40 (2H, t, J=5 Hz), 3.20–3.50 (2H, m), 3.80 (3H, s), 4.05 (2H, t, J=5 Hz), 7.40 (1H, dd, J=1.5, 8 Hz), 7.45 (1H, d, J=1.5 Hz), 7.55 (1H, d, J=8 Hz)

Preparation 17-2)

1-(3-Carboxypropyl)-7-chloro-2,4(1H,3H)-quinazolinedione

NMR (DMSO-d6, δ): 1.70–1.90 (2H, m), 2.40 (2H, t, J=5 Hz), 4.05 (2H, t, J=5 Hz), 7.30 (1H, dd, J=1, 8 Hz), 7.75 (1H, d, J=1Hz), 8.00 (1H, d, J=8 Hz)

The following compounds were obtained in substantially the same manner as that of Preparation 1-4).

Preparation 18-1)

1-(4-Hydroxybutyl)-6-methoxy-2,4(1H,3H)-quinazolinedione

NMR (DMSO-d 6): 1.40–1.70 (4H, m), 3.30–3.50 (2H, m), 3.80 (3H, s), 4.00 (2H, t, J=5 Hz), 7.30–7.50 (3H, m)

Preparation 18-2)

4-Hydroxybutyl)-7-chloro-2,4(1H,3H)-quinazolinedione

NMR (DMSO-d6, δ): 1.40–1.70 (4H, m), 3.30–3.50 (2H, m), 4.00–4.10 (2H, m), 7.30 (1H, dd, J=1.5, 7 Hz), 7.60 (1H, d, J=1.5 Hz), 8.00 (1H, d, J=7 Hz)

The following compounds were obtained in substantially the same manner as that of Preparation 1-5).

Preparation 19-1)

1-(4-Chlorobutyl)-6-methoxy-2,4(1H,3H)-quinazolinedione

NMR (CDCl$_3$, δ): 1.85–1.95 (4H, m), 3.60–3.70 (2H, m), 3.90 (3H, s), 4.10–4.20 (2H, m), 7.20 (1H, d, J=8 Hz), 7.30 (1H, dd, J=2, 8 Hz), 7.65 (1H, d, J=2 Hz)

Preparation 19-2)

1-(4-Chlorobutyl)-7-chloro-2,4(1H,3H)-quinazolinedione

NMR (CDCl$_3$, δ): 1.85–2.0 (4H, m), 3.60–3.70 (2H, m), 4.10–4.20 (2H, m), 7.20–7.30 (2H, m), 8.20 (1H, dd, J=1, 7 Hz), 8.95 (1H, br s)

The following compounds were obtained in substantially the same manner as that of Preparation 3.

Preparation 20-1)

1-[4-{4-(4-Tolyl)-1,2,3,6-tetrahydropyridin-1-yl)-4-oxobutyl]-2,4(1H,3H)-quinazolinedione NMR (CDCl$_3$, δ): 2.00–2.20 (2H, m), 2.35 (3H, s), 2.45–2.65 (4H, m), 3.65–3.75 (1H, m), 3.80–3.90 (1H, m), 4.10–4.30 (4H, m), 5.95–6.10 (1H, m), 7.10–7.35 (5H, m), 7.70–7.80 (2H, m), 8.20–8.40 (2H, m)

Preparation 20-2)

1-[4-{4-(2-Tolyl)piperazin-1-yl}-4-oxobutyl]-2,4(1H,3H)-quinazolinedione

NMR (CDCl$_3$, δ): 2.00–2.20 (2H, m), 2.35 (3H, s), 2.55 (2H, t, J=5 Hz), 2.85–3.00 (4H, m), 3.60 (2H, t, J=4 Hz), 3.80 (2H, t, J=4 Hz), 4.20 (2H, t, J=5 Hz), 6.95–7.05 (2H, m), 7.10–7.30 (5H, m), 7.75 (2H, m), 8.20 (1H, d, J=7 Hz), 8.40 (1H, br s)

Preparation 20-3)

1-[4-(4-Phenylpiperazin-1-yl)-4-oxobutyl]-2,4(1H,3H)-quinazolinedione

Preparation 20-4)

1-[4-{4-(2-Ethoxyphenyl)piperazin-1-yl}-4-oxobutyl]-2,4(1H,3H)-quinazolinedione

NMR (CDCl$_3$, δ): 1.50 (3H, t, J=6 Hz), 2.00–2.20 (2H, m), 2.55 (2H, t, J=5 Hz), 3.05–3.15 (4H, m), 3.60–3.70 (2H, m), 3.80–3.90 (2H, m), 4.10 (2H, q, J=6 Hz), 4.15–4.25 (2H, m), 6.85–7.05 (4H, m), 7.20–7.30 (1H, m), 7.70–7.80 (2H, m), 8.20 (1H, d, J=7 Hz), 8.80 (1H, br s)

Preparation 21

2-[N-{4-(4-Phenyl-1,2,3,6-tetrahydropyridin-1-yl)butyl}-N-ethoxycarbonylamino]-4-chlorobenzamide was obtained in substantially the same manner as that of Preparation 12-3) from 2-[N-{4-(4-phenyl-1,2,3,6-tetrahydropyridn-1-yl)butyl}-N-ethoxycarbonylamino]-4-chlorobenzoic acid, which had been prepared from methyl 2-[N-(4-chlorobutyl)-N-ethoxycarbonylamino-4-chlorobenzoate in substantially the same manner as those of Preparations9-3), 10-3) and 11-3).

Preparation 22

6-Chloro-1-[4-(4-phenyl-1,2,3,6-tetrahydropyridin-1-yl)-4-oxobutyl]-2,4(1H,3H)-quinazolinedione was obtained in substantially the same manner as that of Preparation 4 from 1-[3-carboxy)propyl-6-chloro-2,4(1H,3H)-quinazolinedione, which had been prepared from 2,4(1H,3H)-quinazolinedione in substantially the same manner as those of Preparations-1-1), 1-2) and 1-3).

NMR (CDCl$_3$, δ): 2.40–2.65 (4H, m), 3.50–3.65 (1H, m), 3.65–3.75 (1H, m), 3.85–3.95 (1H, m), 4.10–4.30 (5H, m), 6.00–6.65 (1H, m), 7.20–7.40 (5H, m), 7.65–7.85 (2H, m), 8.15–8.25 (1H, m), 9.25 (1H, br s)

EXAMPLE 1-1)

A mixture of 1-(4-chlorobutyl)-2,4(1H,3H)-quinazolinedione (160 mg), N-(2-propoxyphenyl)piperazine hydrochloride (178 mg), potassium iodide (105 mg), and sodium carbonate (200 mg) in methyl isobutyl ketone (15 ml) was refluxed for 5 hours. After dilution with ethyl acetate, the reaction mixture was washed in turn with water and brine, dried over magnesium sulfate, and evaporated. The residue was chromatographed on silica gel (15 g) eluting with chloroform-methanol (50:1 V/V) to give 1-[4-{4-(2-propoxyphenyl)piperazin-1-yl}butyl]-2,4(1H,3H)-quinazolinedione (266 mg).

mp: ~68° C.

IR (Nujol, ν): 1680, 1600 cm$^{-1}$

NMR (CDCl$_3$, δ): 1.10 (3H, t, J=6 Hz), 1.60–1.90 (6H, m), 2.55 (2H, t, J=5 Hz), 2.60–2.80 (4H, m), 3.10–3.25 (4H, m), 3.95 (2H, t, J=6 Hz), 4.15 (2H, t, J=5 Hz), 6.8–7.00 (4H, m), 7.20–7.30 (1H, m), 7.40 (1H, d, J=7 Hz), 7.70 (1H, dt, J=1, 7 Hz), 8.20 (1H, dd, J=1, 7 Hz), 8.95 (1H, br s)

EXAMPLE 1-2)

A mixture of 1-(4-methanesulfonyloxybutyl)-2,4(1H,3H)-quinazolinedione (312 mg), 4-phenyl-1,2,3,6-tetrahydropyridine (200 mg) and triethylamine (303 mg) was refluxed for 1.5 hours. The reaction mixture was poured into ethyl acetate-water, extracted with ethyl acetate. Combined organic extract was washed in turn with water and brine, dried over magnesium sulfate, and evaporated. The crude residue was washed with hot methanol to give 1-[4-(4-phenyl-1,2,3,6-tetrahydropyridin-1-yl)butyl]-2,4(1H,3H)-quinazolinedione (114 mg) as a powder.

mp: 170°–173.5° C.

IR (Nujol, ν): 1710, 1670, 1600 cm$^{-1}$

NMR (CDCl$_3$, δ): 1.60–1.95 (4H, m), 2.50–2.70 (4H, m), 2.75 (2H, t, J=4.5 Hz), 7.20–7.45 (7H, m), 7.65 (1H, ddd, J=1.5, 6, 6 Hz), 8.20 (1H, dd, J=1.5, 6 Hz)

EXAMPLE 2-1)

To a suspension of 1-[4-{4-(2-nitrophenyl)piperazin-1-yl}-4-oxo-butyl]-2,4(1H,3H)-quinazolinedione (500 mg) in tetrahydrofuran (10 ml) was added 1M borane in tetrahydrofuran (3.42 ml) on an ice-bath. After refluxing for 30 minutes, the reaction mixture was quenched with 1N hydrochloric acid (7 ml), and refluxed for additional 30 minutes. The mixture was made alkaline with saturated aqueous sodium bicarbonate, diluted with ethyl acetate. The organic layer was washed with saturated sodium bicarbonate and brine, dried over magnesium sulfate, and evaporated. The obtained residue was chromatographed on silica gel (20 g) eluting with chloroform-methanol (20:1 V/V) to give crystals. Recrystallization from ethanol gave 1-[4-{4-(2-nitrophenyl)piperazin-1-yl}butyl]-2,4(1H,3H)-quinazolinedione (77 mg).

mp: 164°-165° C.

IR (Nujol, $\nu$): 1700, 1650, 1600 cm$^{-1}$

NMR (CDCl$_3$, $\delta$): 1.60-1.90 (4H, m), 2.45-2.80 (6H, m), 3.00-3.25 (4H, m), 4.15 (2H, t, J=5 Hz), 7.05 (1H, dt, J=1.6 Hz), 7.15 (1H, dd, J=1.6 Hz), 7.20-7.40 (3H, m), 7.50 (1H, dt, J=1.5, 6.5 Hz), 7.70 (1H, dd, J=1.6 Hz), 7.80 (1H, dd, J=1, 6 Hz), 8.20 (1H, dd, J=1.5, 6.5 Hz), 8.65 (1H, br s)

EXAMPLE 2-2)

To a stirred solution of 1-[4-{4-(4-chlorophenyl)-1,2,3,6-tetrahydropyridin-1-yl}butyl-4-oxo]-2,4(1H,3H)-quinazolinedione (400 mg) in dry tetrahydrofuran (5 ml) was added lithium aluminum hydride (77 mg) on an ice-bath. After stirring for 15 minutes, the reaction mixture was quenched with saturated sodium bicarbonate, and diluted with chloroform. After filtration of decomposed materials, the organic filtrate was washed with saturated aqueous sodium bicarbonate and brine dried over magnesium sulfate, and evaporated. The residue was chromatographed on silica gel (15 g). Elution with a mixed solvent of chloroform and methanol (50:1 V/V) gave 1-[4-{4-(4-chlorophenyl)-1,2,3,6-tetrahydropyridin-1-yl}butyl]-2,4(1H,3H)-quinazolinedione (25 mg) after crystallization from diethyl ether.

mp: 162°-166° C.

IR (Nujol, $\nu$): 1680, 1600 cm$^{-1}$

NMR (CDCl$_3$, $\delta$): 1.60-1.90 (4H, m), 2.55-2.70 (4H, m), 2.70-2.85 (2H, m), 3.20-3.30 (2H, m), 4.15 (2H, t, J=5 Hz), 6.05-6.15 (1H, m), 7.20-7.40 (6H, m), 7.65 (1H, dt, J=1, 6.5 Hz), 8.20 (1H, dd, J=1, 6.5 Hz), 8.45 (1H, br s)

EXAMPLE 3

To a solution of 1-[4-{4-(2-nitrophenyl)piperazin-1-yl}butyl]-2,4(1H,3H)-quinazolinedione (90 mg) in ethanol (8 ml) was added tin(II) chloride (159 mg) at 80° C. After stirring for 1 hour at the same temperature, the reaction mixture was quenched with ice and saturated aqueous sodium bicarbonate, and extracted with chloroform. The organic extract was washed with saturated aqueous sodium bicarbonate, dried over magnesium sulfate, and evaporated to give an amorphous. 1-[4-{4-(2-Aminophenyl)piperazin-1-yl)butyl]-2,4(1H,3H)-quinazolinedione (31 mg) was obtained by crystallization of the amorphous from diisopropyl ether.

mp: ~121° C.

IR (Nujol, $\nu$): 1680, 1600 cm

NMR (CDCl$_3$, $\delta$): 1.60-1.90 (4H, m), 2.45-2.80 (6H, m), 2.85-3.10 (4H, m), 3.90-4.05 (2H, m), 4.15 (2H, t, J=6 Hz), 6.70-6.80 (2H, m), 6.90-7.10 (2H, m), 7.20-7.40 (2H, m), 7.70 (1H, dt, J=1.6 Hz), 8.20 (1H, dd, J=1, 6 Hz), 8.60 (1H, br s)

EXAMPLE 4

A mixture of 2-[N-{4-(4-phenyl-1,2,3,6-tetrahydropyridin-1-yl)butyl}-N-ethoxycarbonyl]amino-4-nitrobenzamide (600 mg), and potassium hydroxide (144 mg) in dry ethanol (10 ml) was refluxed for 3 hours. After evaporation of the solvent, the residue was diluted with water, acidified with 3N hydrochloric acid, and extracted with chloroform. The organic layer was washed with brine, dried over magnesium sulfate and evaporated. The crude residue was washed with hot ethanol to give 1-[4-(4-phenyl-1,2,3,6-tetrahydropyridin-1-yl)butyl]-7-nitro-2,4(1H,3H)-quinazolinedione (450 mg) as a powder.

mp: 242°-244° C.

IR [Nujol, $\nu$): 1710, 1680 cm$^{-1}$

NMR (DMSO-d6, $\delta$): 1.65-1.95 (4H, m), 2.70-2.90 (2H, m), 3.15-4.10 (6H, m), 4.15-4.25 (2H, m), 6.20 (1H, br s), 7.30-7.55 (5H, m), 8.05 (1H, dd, J=1.5, 6 Hz), 8.15 (1H, d, J=1.5 Hz), 8.25 (1H, d, J=6 Hz)

EXAMPLE 5

To a stirred suspension of 1-[4-(4-phenyl-1,2,3,6-tetrahydropyridin-1-yl)butyl]-7-nitro-2,4(1H,3H)-quinazolinedione (840 mg) in dry ethanol (30 ml) was added tin(II) chloride (1.90 g) at 80° C. After stirring for 3 hours, the mixture was quenched with 2N potassium hydroxide, diluted with chloroform. The organic layer was decanted and the residue was washed with chloroform. Combined organic layer was dried over magnesium sulfate and evaporated. 1-[4-(4-Phenyl-1,2,3,6-tetrahydropyridin-1-yl)butyl]-7-amino-2,4(1H,3H)-quinazolinedione hydrochloride (546 mg) as a crystal was obtained by recrystallization from 10% hydrogen chloride in methanol.

mp: 297°-299° C.

IR (Nujol, $\nu$): 1680, 1600 cm$^{-1}$

NMR (DMSO-d6, $\delta$): 1.60-1.95 (4H, m), 2.65-3.00 (2H, m), 3.10-3.35 (3H, m), 3.55-4.20 (5H, m), 6.20 (1H, br s), 6.50 (1H, d, J=7 Hz), 6.55 (1H, br s), 7.30-7.55 (5H, m), 7.70 (1H, d, J=7 Hz)

EXAMPLE 6

A mixture of 1-[4-(4-phenyl-1,2,3,6-tetrahydropyridin-1-yl)butyl]-7-methoxy-2,4(1H,3H)-quinazolinedione (300 mg) and 47% hydrobromic acid (3.8 ml) in acetic acid (6 ml) was refluxed for 24 hours. After dilution with water, precipitates were collected. A crude crystalline material was recrystallized from ethanol to give 1-[4-(4-phenyl-1,2,3,6-tetrahydropyridin-1-yl)butyl]-7-hydroxy-2,4(1H,3H)-quinazolinedione hydrobromide (140 mg).

mp: 278°-280° C.

IR (Nujol, $\nu$): 1690, 1660, 1600 cm$^{-1}$

NMR (DMSO-d6, $\delta$): 1.60-1.90 (4H, m), 2.75-2.85 (2H, m), 3.20-3.40 (4H, m), 3.65-4.10 (4H, m), 6.15-6.25 (1H, m), 6.70-6.80 (2H, m), 7.35-7.55 (5H, m), 7.85 (1H, d, J=7 Hz), 9.60 (1H, br s)

EXAMPLE 7

5-Chloro-1-[4-[4-phenyl-1,2,3,6-tetrahydropyridin-1-yl)butyl]-2,4(1H,3H)-quinazolinedione was obtained in 62.2% yield in substantially the same manner as that of

EXAMPLE 4 mp: ~238° C.

IR (Nujol, $\nu$): 1690, 1590 cm$^{-1}$

NMR (CDCl$_3$, $\delta$): 1.70–2.20 (4H, m), 2.70–3.30 (6H, m), 3.50–3.80 (2H, m), 4.15 (2H, t, J=6 Hz), 6.00 (1H, br s), 7.25–7.45 (7H, m), 7.60 (1H, t, J=7 Hz)

EXAMPLE 8

A mixture of 2-[4-(4-phenyl-1,2,3,6-tetrahydropyridin-1-yl)butylamino]-6-nitrobenzamide (300 mg) and N,N'-carbonyldiimidazole (554 mg) in dioxane (3 ml) was stirred for 2 hours at 150° C. The solvent was removed during the reaction. The residue was crystalized from a mixture of ethanol and ether. The crude crystalline materials were collected, washed with methylene chloride, and recrystallized from ethanol to afford 1-[4-(4-phenyl-1,2,3,6-tetrahydropyridin-1-yl)butyl]-5-nitro-2,4(1H,3H)-quinazolinedione (265 mg).

mp: 182° C. (dec.)

IR (Nujol): 1710, 1680, 1610, 1530 cm$^{-1}$

NMR (DMSO-d$_6$, $\delta$): 1.50–1.55 (4H, m), 2.40–2.55 (2H, m), 2.60–2.70 (2H, m), 3.00–3.10 (2H, m), 3.30–3.40 (2H, m), 3.90–4.00 (2H, m), 6.15–6.20 (1H, m), 6.40 (1H, d, J=7 Hz), 6.50 (1H, d, J=7 Hz), 7.20–7.50 (8H, m)

EXAMPLE 9

1-[4-(4-Phenyl-1,2,3,6-tetrahydropyridin-1-yl)butyl]-5-amino-2,4(1H,3H)-quinazolinedione was obtained in substantially the same manner as that of Example 5.

mp: 204° C. (dec.)

IR (Nujol): 1680, 1580, 1500 cm$^{-1}$

NMR (DMSO-d$_6$, $\delta$): 1.50–1.55 (4H, m), 2.40–2.55 (2H, m), 2.60–2.70 (2H, m), 3.00–3.10 (2H, m), 3.30–3.40 (2H, m), 3.90–4.00 (2H, m), 6.15–6.20 (1H, m), 6.40 (1H, d, J=7 Hz), 6.50 (1H, d, J=7 Hz), 7.20–7.50 (8H, m)

EXAMPLE 10

To a solution of 5-nitro-1-[4-(4-phenyl-1,2,3,6-tetrahydropyridin-1-yl)butyl]-2,4(1H,3H)-quinazolinedione (500 mg) in a mixture of chloroform (9 ml) and methanol (1 ml) was added 2N solution of sulfuric acid in methanol (1.19 ml) at 0° C. After evaporation of the solvent, the crystalline residue was recrystallized from 10% water in ethanol (30 ml) to give 5-nitro-1-[4-(4-phenyl-1,2,3,6-tetrahydropyridin-1-yl)butyl]-2,4(1H,3H)-quinazolinedione sulfate (497 mg) as pale brown crystals.

mp: 187°–188° C.

IR (Nujol): 3540, 1700, 1685, 1605 cm$^{-1}$

NMR (DMSO-d$_6$, $\delta$): 1.58–1.90 (4H, m), 2.72 (2H, br s), 3.12 (2H, t, J=5 Hz), 3.45 (2H, br s), 3.80 (2H, br s), 4.10 (2H, d, J=5 Hz), 6.18 (1H, s), 7.28–7.55 (6H, m), 7.73 (1H, d, J=8 Hz), 7.91 (1H, t, J=8 Hz), 9.50 (1H, br s)

The following compounds were obtained in substantially the same manner as that of Example 1-2).

EXAMPLE 11-1)

1-[4-{4-(2-Chlorophenyl)piperazin-1-yl}butyl]-2,4(1H,3H)-quinazolinedione mp: 176°–178° C.

IR (Nujol): 1700, 1680, 1610 cm$^{-1}$

NMR (CDCl$_3$, $\delta$): 1.60–1.90 (4H, m), 2.50–2.85 (6H, m), 3.00–3.30 (4H, m), 4.15 (2H, t, J=6 Hz), 6.90–7.10 (2H, m), 7.15–7.40 (5H, m), 7.70 (1H, dt, J=1, 7 Hz), 8.20 (1H, dd, J=1, 7 Hz), 8.80 (1H, br s)

EXAMPLE 11-2)

1-[4-{4-(2-Methoxyphenyl)piperazin-1-yl)butyl]-2,4(1H,3H)-quinazolinedione mp: ~110° C.

IR (Nujol): 1670,.1600 cm$^{-1}$

NMR (CDCl$_3$, $\delta$): 1.60–2.10 (4H, m), 2.50–2.60 (2H, t, J=5 Hz), 2.65–2.80 (4H, m), 3.10–3.25 (4H, m), 3.90 (3H, s), 4.15 (2H, t, J=5 Hz), 6.85–7.05 (4H, m), 7.20–7.30 (1H, m), 7.35 (1H, d, J=7 Hz), 7.70 (1H, dt, J=1, 7 Hz), 8.25 (1H, dd, J=1, 7 Hz)

The following compounds were obtained substantially the same manner as that of Example 1-1).

EXAMPLE 11-3)

1-[4-{4-(2-Methoxyphenyl)piperazin-1-yl)butyl]-6-methoxy-2,4(1H,3H)-quinazolinedione mp: 198°–200° C.

IR (Nujol): 1700, 1660, 1580 cm$^{-1}$

NMR (CDCl$_3$, $\delta$): 1.60–1.90 (4H, m), 2.50 (2H, t, J=5 Hz), 4.15 (2H, t, J=6 Hz), 6.85–7.05 (4H, m), 7.25–7.35 (2H, m), 7.65 (1H, d, J=1.5 Hz), 8.75 (1H, br s)

EXAMPLE 11-4)

1-[4-{4-(2-Chlorophenyl)piperazin-1-yl}butyl]-6-methoxy-2,4(1H,3H)-quinazolinedione mp: 204°–206° C.

IR (Nujol): 1710, 1660 cm$^{-1}$

NMR (CDCl$_3$, $\delta$): 1.60–1.90 (4H, m), 2.55 (2H, t, J=6 Hz), 2.60–2.75 (4H, m), 3.05–3.20 (4H, m), 3.90 (3H, s), 4.15 (2H, t, J=6 Hz), 6.95–7.10 (2H, m), 7.20–7.30 (3H, m), 7.35 (1H, dd, J=1, 7 Hz), 7.60–7.70 (1H, m), 8.85 (1H, br s)

EXAMPLE 11-5)

1-[4-{4-(2-Methoxyphenyl)piperazin-1-yl}butyl]-7-chloro-2,4(1H,3H)-quinazolinedione mp: 190°–191° C.

IR (Nujol): 1700, 1680, 1600 cm$^{-1}$

NMR (CDCl$_3$, $\delta$): 1.60–1.90 (4H, m), 2.55 (2H, t, J=5 Hz), 2.65–2.80 (4H, m), 3.10–3.20 (4H, m), 3.90 (3H, s), 4.15 (2H, t, J=5 Hz), 6.85–7.05 (4H, m), 7.25 (1H, dd, J=1.5, 7 Hz), 7.35 (1H, d, J=1.5 Hz), 8.15 (1H, d, J=7 Hz)

EXAMPLE 11-6)

1-[4-(4-(2-Chlorophenyl)piperazin-1-yl}butyl]-7-chloro-2,4(1H,3H)-quinazolinedione mp: 174°–176° C.

IR (Nujol): 1690, 1600 cm$^{-1}$

NMR (CDCl$_3$, $\delta$): 1.50–1.90 (4H, m), 2.50–2.85 (6H, m), 3.05–3.30 (4H, m), 4.15 (2H, t, J=5 Hz), 6.95–7.10 (2H, m), 7.20–7.30 (2H, m), 7.30–7.40 (2H, m), 8.15 (1H, d, J=8 Hz), 8.55 (1H, br s)

EXAMPLE 11-7)

1-[4-(4-Phenyl-1,2,3,6-tetrahydropyridin-1-yl)butyl]-7-hydroxy-2,4(1H,3H)-quinazolinedione hydrobromide mp: 278°–280° C.

EXAMPLE 11-8)

1-[4-(4-Phenyl-1,2,3,6-tetrahydropyridin-1-yl)butyl]-5-nitro-2,4(1H,3H)-quinazolinedione mp: 182° C. (dec.)

The following compounds were obtained in substantially the same manner as that of Example 2-1).

EXAMPLE 12-1)

1-[4-{4-(4-Tolyl)-1,2,3,6-tetrahydropyridin-1-yl}butyl]-2,4(1H,3H)-quinazolinedione
mp: 152°-156° C.
IR (Nujol): 1710, 1670, 1600 cm$^{-1}$
NMR (CDCl$_3$, δ): 1.70-1.90 (4H, m), 2.35 (3H, s), 2.55-2.70 (4H, m), 2.75-2.85 (2H, m), 3.20-3.30 (2H, m), 4.15 (2H, t, J=5 Hz), 6.00-6.10 (1H, m), 7.10-7.35 (5H, m), 7.45 (1H, d, J=7 Hz), 7.65 (1H, dt, J=1, 7 Hz), 8.20 (1H, dd, J=1, 7 Hz), 8.45 (1H, br s)

EXAMPLE 12-2)

1-[4-{4-(2-Tolyl)piperazin-1-yl}butyl]-2,4(1H,3H)-quinazolinedione
mp: 74°-85° C.
IR (Nujol): 1700, 1600 cm$^{-1}$
NMR (CDCl$_3$, δ): 1.60-1.90 (4H, m), 2.30 (3H, s), 2.50 (2H, t, J=5 Hz), 2.60-2.70 (4H, m), 2.95 (4H, t, J=4 Hz), 4.15 (2H, t, J=5 Hz), 6.95-7.05 (2H, m), 7.10-7.40 (4H, m), 7.70 (1H, dt, J=1, 7 Hz), 8.20 (1H, dd, J=1.5, 7 Hz), 8.75 (1H, br s)

EXAMPLE 12-3)

1-[4-(4-Phenylpiperazin-1-yl)butyl]-2,4(1H,3H)-quinazolinedione
mp: 164°-167° C.
IR (Nujol): 1710, 1670, 1600 cm$^{-1}$
NMR (CDCl$_3$, δ): 1.60-1.90 (4H, m), 2.55 (2H, t, J=4 Hz), 2.60-2.75 (4H, m), 3.25 (4H, t, J=4 Hz), 4.15 (2H, t, J=6 Hz), 6.80-7.00 (3H, m), 7.20-7.40 (4H, m), 7.70 (1H, dt, J=1, 7 Hz), 8.20 (1H, dd, J=1, 7 Hz), 8.65 (1H, br s)

EXAMPLE 12-4)

1-[4-{4-(2-Ethoxyphenyl)piperazin-1-yl}butyl]-2,4(1H,3H)-quinazolinedione
mp: ~85° C.
IR (Nujol): 1680, 1600 cm$^{-1}$
NMR (CDCl$_3$, δ): 1.45 (3H, t, J=6 Hz), 1.60-1.90 (4H, m), 2.50 (2H, t, J=5 Hz), 2.65-2.80 (4H, m), 3.10-3.25 (4H, m), 4.00-4.20 (4H, m), 6.80-7.00 (4H, m), 7.30 (1H, t, J=7 Hz), 7.40 (1H, d, J=7 Hz), 7.70 (1H, dt, J=1.5, 7 Hz), 8.20 (1H, dd, J=1.5, 7 Hz), 8.75 (1H, br s)

EXAMPLE 12-5)

6-Chloro-1-[4-(4-phenyl-1,2,3,6-tetrahydropyridin-1-yl)butyl]-2,4(1H,3H)-quinazolinedione
mp: 159° C. (dec.)
IR (Nujol): 1680, 1600 cm$^{-1}$
NMR (CDCl$_3$, δ): 1.65-1.90 (4H, m), 2.55-2.70 (4H, m), 2.70-2.85 (2H, m), 3.20-3.30 (2H, m), 4.05-4.20 (2H, m), 6.05-6.15 (1H, m), 7.20-7.45 (6H, m), 7.55 (1H, dd, J=1.5, 8 Hz), 8.15 (1H, d, J=1.5 Hz)

EXAMPLE 12-6)

1-[4-(4-Phenyl-1,2,3,6-tetrahydropyridin-1-yl)butyl]-7-hydroxy-2,4(1H,3H)-quinazolinedione hydrobromide
mp: 278°-280° C.

EXAMPLE 12-7)

1-[4-(4-Phenyl-1,2,3,6-tetrahydropyridin-1-yl)butyl]-5-nitro-2,4(1H,3H)-quinazolinedione
mp: 182° C. (dec.)

The following compounds were obtained in substantially the same manner as that of Example 4.

EXAMPLE 13-1)

1-[4-(4-Phenyl-1,2,3,6-tetrahydropyridin-1-yl)butyl]-6-ethoxy-2,4(1H,3H)-quinazolinedione
mp: 170°-172° C.
IR (Nujol): 1690, 1650, 1580 cm$^{-1}$
NMR (CDCl$_3$, δ): 1.40 (3H, t, J=6 Hz), 1.65-1.90 (4H, m), 2.55-2.70 (4H, m), 2.70-2.80 (2H, m), 3.15-3.25 (2H, m), 4.00 (2H, q, J=6 Hz), 4.15 (2H, t, J=5 Hz), 6.05-6.15 (1H, m), 7.15-7.40 (7H, m), 7.60 (1H, d, J=2 Hz), 8.60 (1H, br s)

EXAMPLE 13-2)

1-[4-(4-Phenyl-1,2,3,6-tetrahydropyridin-1-yl)butyl]-6-methoxy-2,4(1H,3H)-quinazolinedione
mp: 192°-194° C.
IR (Nujol): 1670 cm$^{-1}$
NMR (CDCl$_3$, δ): 1.70-1.90 (4H, m), 2.55-2.70 (4H, m), 2.80 (2H, t, J=4 Hz), 3.20-3.30 (2H, m), 3.80 (3H, s), 4.15 (2H, t, J=6 Hz), 6.05-6.15 (1H, m), 7.20-7.45 (7H, m), 7.60 (1H, d, J=2 Hz), 8.60 (1H, br s)

EXAMPLE 13-3)

1-[4-(4-Phenyl-1,2,3,6-tetrahydropyridin-1-yl)butyl]-8-chloro-2,4(1H,3H)-quinazolinedione
mp: 194°-197° C.
IR (Nujol): 1680, 1600 cm$^{-1}$
NMR (DMSO-d$_6$, δ): 1.60-1.90 (4H, m), 2.60-2.80 (2H, m), 2.90-3.75 (6H, m), 4.25-4.40 (2H, m), 6.20 (1H, br s), 7.25-7.50 (6H, m), 7.85 (1H, dd, J=1, 6 Hz), 8.05 (1H, dd, J=1, 6 Hz)

EXAMPLE 13-4)

1-[4-(4-Phenyl-1,2,3,6-tetrahydropyridin-1-yl)butyl]-7-methoxy-2,4(1H,3H)-quinazolinedione
mp: 171°-173° C.
IR (Nujol): 1690, 1610 cm$^{-1}$
NMR (DMSO-d$_6$, δ): 1.70-1.90 (4H, m), 2.60-2.70 (4H, m), 2.85 (2H, t, J=5 Hz), 3.25-3.35 (2H, m), 3.85 (3H, s), 4.10 (2H, t, J=5.5 Hz), 6.05-6.10 (1H, m), 6.70 (1H, d, J=2 Hz), 6.80 (1H, dd, J=2, 8 Hz), 7.25-7.40 (5H, m), 8.15 (1H, d, J=8 Hz), 8.45 (1H, br s)

EXAMPLE 13-5)

1-[4-(4-Phenyl-1,2,3,6-tetrahydropyridin-1-yl)butyl]-6,7-dimethoxy-2,4(1H,3H)-quinazolinedione
IR (Nujol): 1680, 1620 cm$^{-1}$
NMR (CDCl$_3$, δ): 1.85-2.00 (4H, m), 2.75-2.85 (2H, m), 2.85-2.95 (2H, m), 3.10 (2H, t, J=6 Hz), 3.95 (3H, s), 4.05 (3H, s), 4.20 (2H, t, J=7 Hz), 6.00-6.05 (1H, m), 6.70 (1H, s), 7.25-7.40 (5H, m), 7.60 (1H, s)

EXAMPLE 13-6)

1-[4-(4-Phenyl-1,2,3,6-tetrahydropyridin-1-yl)butyl]-7-chloro-2,4(1H,3H)-quinazolinedione
mp: 152°-154° C.
IR (Nujol): 1680, 1600 cm$^{-1}$
NMR (CDCl$_3$, δ): 1.60-1.90 (4H, m), 2.55-2.70 (4H, m), 2.75-2.85 (2H, t, J=5 Hz), 3.20-3.30 (2H, m), 4.15 (2H, t, J=6 Hz), 6.05-6.15 (1H, m), 7.20-7.45 (7H, m), 8.15 (1H, d, J=7 Hz)

EXAMPLE 13-7)

1-[4-(4-Phenyl-1,2,3,6-tetrahydropyridin-1-yl)butyl]-6-nitro-2,4(1H,3H)-quinazolinedione
mp: 194° C. (dec.)
IR (Nujol): 1710, 1670, 1610 cm$^{-1}$
NMR (DMSO-d$_6$, δ): 1.65-1.75 (4H, m), 2.40-2.60 (4H, m), 2.60-2.70 (2H, m), 3.10-3.20 (2H, m), 4.05-4.20

(2H, m), 6.20 (1H, br s), 7.20–7.50 (5H, m), 7.80 (1H, d, J=8 Hz), 8.40 (1H, dd, J=2, 8 Hz), 8.65 (1H, d, J=2 Hz)

EXAMPLE 13-8)

1-[4-[4-Phenyl-1,2,3,6-tetrahydropyridin-1-yl)butyl]-7-hydroxy-2,4(1H,3H)-quinazolinedione hydrobromide
mp: 278°–280° C.

EXAMPLE 13-9)

1-[4-(4-Phenyl-1,2,3,6-tetrahydropyridin-1-yl)butyl]-5-nitro-2,4(1H,3H)-quinazolinedione
mp: 182° C. (dec.)

The following compounds were obtained in substantially the same manner as that of Example 6.

EXAMPLE 14-1)

1-[4-(4-Phenyl-1,2,3,6-tetrahydropyridin-1-yl)butyl]-6-hydroxy-2,4(1H,3H)-quinazolinedione hydrobromide
mp: 274°–276° C.
IR (Nujol): 1670, 1480 cm$^{-1}$
NMR (DMSO-d$_6$, δ): 1.60–1.90 (4H, m), 2.75–2.90 (2H, m), 3.20–3.40 (3H, m), 3.60–3.90 (2H, m), 3.90–4.10 (3H, m), 6.20 (1H, br s), 7.20 (1H, dd, J=2, 8 Hz), 7.30–7.55 (7H, m), 9.60 (1H, br s), 9.80 (1H, s)

EXAMPLE 14-2)

1-[4-(4-Phenyl-1,2,3,6-tetrahydropyridin-1-yl)butyl]-6,7-dihydroxy-2,4(1H,3H)-quinazolinedione hydrobromide
mp: 280°–282° C.
IR (Nujol): 3650–3100, 1690, 1660, 1620 cm$^{-1}$
NMR (DMSO-d$_6$, δ): 1.60–1.90 (4H, m), 2.75–2.85 (2H, m), 3.20–3.40 (5H, m), 3.60–3.90 (2H, m), 3.90–4.05 (3H, m), 6.20 (1H, br s), 6.80 (1H, s), 7.30–7.55 (6H, m), 9.60 (1 or 2H, br s)

EXAMPLE 14-3)

1-[4-(4-Phenyl-1,2,3,6-tetrahydropyridin-1-yl)butyl]-5-hydroxy-2,4(1H,3H)-quinazolinedione
mp: 262°–264° C.
IR (Nujol): 1690, 1650, 1620, 1260 cm$^{-1}$
NMR (CDCl$_3$, δ): 1.60–1.95 (4H, m), 2.75–2.90 (2H, m), 3.20–4.00 (6H, m), 4.10 (2H, t, J=5 Hz), 6.20 (1H, br s), 6.70 (1H, d, J=7 Hz), 6.95 (1H, d, J=7 Hz), 7.35–7.70 (6H, m)

EXAMPLE 15

1-[4-(4-Phenyl-1,2,3,6-tetrahydropyridin-1-yl)butyl]-6-amino-2,4(1H,3H)-quinazolinedione hydrochloride was obtained in substantially the same manner as that of Example 5.
mp: ~210° C.
IR (Nujol): 1680, 1620 cm$^{-1}$
NMR (DMSO-d$_6$, δ): 1.60–1.95 (4H, m), 2.70–3.00 (2H, m), 3.00–3.90 (4H, m), 3.90–4.20 (4H, m), 6.20 (1H, br s), 7.30–7.65 (7H, m), 7.85 (1H, d, J=1Hz)

EXAMPLE 16-1)

1-[4-(4-Phenyl-1,2,3,6-tetrahydropyridin-1-yl)butyl]-5-(imidazol-1-yl)-2,4(1H,3H)-quinazolinedione was obtained from 2-[N-{4-(4-phenyl-1,2,3,6-tetrahydropyridin-1-yl)butylamino]-6-fluorobenzamide in substantially the same manner as that of Example 8.
IR (Nujol): 1700, 1670, 1600, 1490 cm$^{-1}$
NMR [DMSO-d$_6$, δ): 1.55–1.80 (4H, m), 2.40–2.60 (2H, m), 2.60–2.70 (2H, m), 3.05–3.20 (2H, m), 3.30–3.55 (2H, m), 4.05–4.20 (2H, m), 6.20 (1H, br s), 7.00 (1H, s), 7.10–7.20 (1H, m), 7.20–7.50 (6H, m), 7.70 (3H, br s)

EXAMPLE 16-2)

A mixture of 2-[N-{4-(4-phenyl-1,2,3,6-tetrahydropyridin-1-yl)butylamino-6-fluorobenzamide (900 mg), trichloromethyl chloroformate (1.5 ml) and active charcoal (catalytic amounts) in dioxane (20 ml) was stirred for 1 hour at 80° C. The solvent was removed in vacuo. The residue was dissolved in 10% hydrogen chloride-methanol, then the solution was filtered. After evaporation of the filtrate, the residue was crystallized from ethanol-ether. The crude crystals were collected, and washed with hot ethanol to afford 1-[4-(4-phenyl-1,2,3,6-tetrahydropyridin-1-yl)butyl]-5-fluoro-2,4(1H,3H)-quinazolinedione hydrochloride (80 mg).
mp: 276° C. (dec.)
IR (Nujol): 1680, 1610 cm$^{-1}$
NMR DMSO-d$_6$, δ): 1.60–1.90 (4H, m), 2.70–2.90 (2H, m), 3.15–4.20 (8H, m), 6.20 (1H, br s), 7.10 (1H, dd, J=7 Hz), 7.30–7.60 6H, m), 7.75 (1H, dt, J=4, 7 Hz)

The following compounds were obtained in substantially the same manner as that of Example 16-2).

EXAMPLE 16-3)

1-[4-(4-Phenyl-1,2,3,6-tetrahydropyridin-1-yl)butyl]-5-methoxy-2,4(1H,3H)-quinazolinedione
mp: 219°–221° C.
IR (Nujol): 1670, 1590, 1260 cm$^{-1}$
NMR (CDCl$_3$, δ): 1.50–1.70 (4H, m), 2.40–2.55 (4H, m), 3.05–3.15 (2H, m), 3.80 (3H, s), 4.00–4.10 (2H, m), 6.20 (1H, br s), 6.85 (1H, d, J=6 Hz), 7.10 (1H, d, J=6 Hz), 7.20–7.60 (6H, m)

EXAMPLE 16-4)

1-[4-(4-Phenyl-1,2,3,6-tetrahydropyridin-1-yl)butyl]-5-methyl-2,4(1H,3H)-quinazolinedione
mp: 175°–177° C.
IR (Nujol): 1680, 1590, 1490 cm$^{-1}$
NMR (CDCl$_3$, δ): 1.70–2.00 (4H, m), 2.55–2.70 (4H, m), 2.70–2.85 (5H, m), 3.20–3.30 (2H, m), 4.15 (2H, t, J=5 Hz), 6.05–6.15 (1H, m), 7.00 (1H, d, J=7 Hz), 7.20–7.50 (7H, m)

EXAMPLE 16-5)

1-[4-(4-Phenyl-1,2,3,6-tetrahydropyridin-1-yl)butyl]-5-nitro-2,4(1H,3H)-quinazolinedione
mp: 182° C. (dec.)

EXAMPLE 17

A mixture of 1-[4-(4-phenyl-1,2,3,6-tetrahydropyridin-1-yl)butyl]-7-amino-2,4(1H,3H)-quinazolinedione hydrochloride (70 mg), methanesulfonyl chloride (0.02 ml) potassium carbonate (50 mg) in dimethylformamide (1 ml) was stirred for 2 hours at room temperature. The reaction mixture was poured into ice-water, and extracted with ethyl acetate. The extract was washed in turn with water and brine, dried over magnesium sulfate, and evaporated. The crude residue was washed with hot ethanol, then treated with 10% hydrogen chloride-methanol, and evaporated 1-[4-(4-phenyl-1,2,3,6-tetrahydropyridin-1-yl)-butyl]-7-methanesulfonylamino-2,4(1H,3H)-quinazolinedione hydrochloride (18 mg) as a crystal was obtained by recrystallization from ethanol.
mp: 254° C. (dec.)
IR (Nujol): 1680, 1610, 1590 cm$^{-1}$
NMR (DMSO-d$_6$, δ): 1.65–2.05 (4H, m), 2.70–2.90 (2H, m), 3.15–3.50 (5H, m), 3.60–4.15 (6H, m), 6.20 (1H, br s), 7.45–7.55 (5H, m), 7.95 (1H, br s), 8.05 (1H, d, J=8 Hz), 9.05–9.20 (1H, m)

What is claimed is:

1. A compound of the formula:

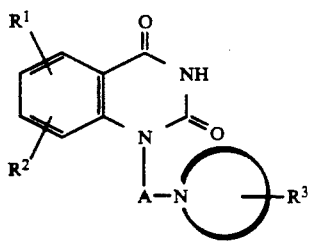

in which
R¹ and R² are each hydrogen, halogen, nitro, amino, protected amino, hydroxyamino, lower alkoxy, lower alkyl, hydroxy, sulfamoyl, carboxy, protected carboxy, carbamoyl, mercapto, lower alkylthio or imidazolyl, R³ is aryl which is unsubstituted or substituted by a substituent selected from the group consisting of halogen, lower alkyl, nitro and amino, A is lower alkylene, and the formula:

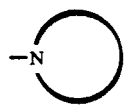

is N-containing heterocyclic group selected from the group consisting of unsaturated 5- or 6-membered hetereomonocyclic group containing 1 to 4 nitrogen atom(s), unsaturated 5- or 6-membered heteromonocyclic group containing 1 to 2 oxygen atoms(s) and 1 to 3 nitrogen atoms(s), saturated 5- or 6-membered heteromonocyclic group containing 1 to 2 oxygen atom(s) and 1 to 3 nitrogen atom(s), unsaturated 5- or 6-membered heteromonocyclic group containing 1 to 2 sulfur atom(s) and 1 to 3 atom(s), and saturated 5- or 6-membered heteromonocyclic group containing 1 to 2 sulfur atom(s) and 1 to 3 nitrogen atom(s), or pharmaceutically acceptable salts thereof.

2. The compound of claim 1, wherein
R¹ and R² are each hydrogen, halogen, nitro, amino, acylamino, hydroxyamino, lower alkoxy, lower alkyl, hydroxy, sulfamoyl, carboxy, esterified carboxy, carbamoyl, mercapto, lower alkylthio or imidazolyl, R³ is phenyl which is unsubstituted or substituted by one to three substituent(s) selected from the group consisting of halogen, lower alkyl, nitro and amino, and the formula:

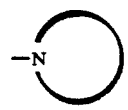

is unsaturated 5- or 6-membered heteromonocyclic group containing 1 to 4 nitrogen atom(s), unsaturated 5- or 6-membered heteromonocyclic group containing 1 to 2 oxygen atom(s) and 1 to 3 nitrogen atom(s), saturated 5- or 6-membered heteromonocyclic group containing 1 to 2 oxygen atom(s) and 1 to 3 nitrogen atom(s), unsaturated 5- or 6-membered heteromonocyclic group containing 1 to 2 sulfur atom(s) and 1 to 3 nitrogen atom(s), or saturated 5- or 6-membered heteromonocyclic group containing 1 to 2 sulfur atom(s) and 1 to 3 nitrogen atom(s).

3. The compound of claim 2, wherein the formula:

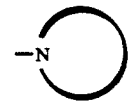

is unsaturated 5- or 6-membered heteromonocyclic group containing 1 to 4 nitrogen atom(s).

4. The compound of claim 3, wherein the formula:

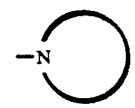

is pyrrol-1-yl, pyrrolin-1-yl, imidazol-1-yl, pyrazol-1-yl, tetrahydropyridyl, triazolyl, tetrazolyl, dihydrotriazinyl, oxadiazinyl, morpholin-4-yl, thiazolinyl, or thiazolidin-1-yl.

5. The compound of claim 4, wherein
R¹ and R² are each hydrogen, halogen, nitro, amino, lower alkanesulfonylamino, lower alkoxy, lower alkyl, hydroxy or imidazolyl, and the formula:

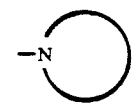

is 1,2,3,6-tetrahydropyridin-1-yl.

6. The compound of claim 5, wherein
R¹ and R² are each hydrogen, halogen, nitro, amino, $C_1$–$C_4$ alkanesulfonylamino, $C_1$–$C_4$ alkoxy, $C_1$–$C_4$ alkyl, hydroxy or imidazol-1-yl, R³ is phenyl which is unsubstituted or substituted by a substituent selected from the group consisting of halogen, $C_1$–$C_4$ alkyl, nitro and amino, and A is $C_1$–$C_4$ alkylene.

7. The compound of claim 6, wherein
R¹ and R² are each hydrogen, chlorine, fluorine, nitro, amino, methanesulfonylamino, methoxy, ethoxy, methyl, hydroxy or imidazolyl, R³ is phenyl which is unsubstituted or substituted by a substituent selected from the group consisting of chloro, methyl, nitro and amino, and A is tetramethylene.

8. A method for the treatment of dopamine receptor mediated diseases which comprises administering an effective amount of a compound of claim 1 to a human being or body.

9. The compound of claim 7, wherein the formula:

is 1,2,3,6-tetrahydropyridin-1-yl.

10. The compound of claim 9, which is

1-[4-(4-phenyl-1,2,3,6-tetrahydropyridin-1-yl)butyl]-7-nitro-2,4(1H,3H)-quinazolinedione, 1-[4-(4-phenyl-1,2,3,6-tetrahydropyridin-1-yl)butyl]-7-hydroxy-2,4(1H,3H)-quinazolinedione hydrobromide, 1-[4-(4-phenyl-1,2,3,6-tetrahydropyridin-1-yl)butyl]-5-nitro-2,4(1H,3H)-quinazolinedione or sulfate thereof, 1-[4-(4-phenyl-1,2,3,6-tetrahydropyridin-1-yl)butyl]-6-nitro-2,4(1H,3H)-quinazolinedione, 1-[4-(4-phenyl-1,2,3,6-tetrahydropyridin-1-yl)butyl]-6-hydroxy-2,4(1H,3H)-quinazolinedione or hydrobromide thereof, 1-[4-(4-phenyl-1,2,3,6-tetrahydropyridin-1-yl)butyl]-6,7-dihydroxy-2,4(1H,3H)-quinazolinedione or hydrobromide thereof, or 1-[4-(4-phenyl-1,2,3,6-tetrahydropyridin-1-yl)butyl]-5-hydroxy-2,4(1H,3H)-quinazolinedione.

11. A pharmaceutical composition comprising, as an active ingredient, an effective amount of a compound of claim 1 in admixture with a pharmaceutically acceptable carrier or excipient.

* * * * *